United States Patent
Braga et al.

(10) Patent No.: US 10,406,036 B2
(45) Date of Patent: Sep. 10, 2019

(54) APPARATUS FOR VACUUM BRIDGING AND/OR EXUDATE COLLECTION

(71) Applicant: Smith & Nephew, Inc., Memphis, TN (US)

(72) Inventors: Richard M. Braga, North Easton, MA (US); E. David Fink, Franklin, MA (US); David G. Heagle, Taunton, MA (US); Ronald F. Vitaris, Worcester, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/856,007

(22) Filed: Dec. 27, 2017

(65) Prior Publication Data

US 2018/0133064 A1    May 17, 2018

Related U.S. Application Data

(60) Division of application No. 13/552,000, filed on Jul. 18, 2012, now abandoned, which is a continuation of application No. 12/486,858, filed on Jun. 18, 2009, now abandoned.

(51) Int. Cl.
*A61M 1/00* (2006.01)
*A61F 13/00* (2006.01)

(52) U.S. Cl.
CPC ........ *A61F 13/00068* (2013.01); *A61F 13/00* (2013.01); *A61M 1/0088* (2013.01)

(58) Field of Classification Search
CPC .. A61F 13/00068; A61F 13/00; A61M 1/0088
See application file for complete search history.

(56) References Cited

U.S. PATENT DOCUMENTS

| | | | |
|---|---|---|---|
| 1,585,104 | A | 5/1926 | Montgomery |
| 2,736,317 | A | 2/1956 | Alexander |
| 3,026,874 | A | 3/1962 | Stevens |
| 3,042,041 | A | 7/1962 | Jascalevich |
| 3,367,332 | A | 2/1968 | Groves |
| 3,486,504 | A | 12/1969 | Austin, Jr. |
| 3,520,300 | A | 7/1970 | Flower, Jr. |
| 3,568,675 | A | 3/1971 | Harvey |
| 3,572,340 | A | 3/1971 | Lloyd et al. |

(Continued)

FOREIGN PATENT DOCUMENTS

| | | |
|---|---|---|
| AU | 674837 B2 | 1/1997 |
| DE | 3 907 007 | 9/1990 |

(Continued)

OTHER PUBLICATIONS

US 6,216,701 B1, 04/2001, Heaton et al. (withdrawn)

(Continued)

*Primary Examiner* — Tatyana Zalukaeva
*Assistant Examiner* — Sara A Sass
(74) *Attorney, Agent, or Firm* — Knobbe, Martens, Olson & Bear LLP

(57) ABSTRACT

An apparatus for promoting the healing of an exuding wound includes a cover layer for positioning over a wound to define a reservoir over the wound. An exudate conduit having a fibrous core includes a plurality of fibers communicates with the reservoir for wicking fluids away from the wound.

24 Claims, 9 Drawing Sheets

(56) References Cited

U.S. PATENT DOCUMENTS

| | | | |
|---|---|---|---|
| 3,712,298 A | 1/1973 | Snowdon et al. | |
| 3,753,439 A | 8/1973 | Brugarolas et al. | |
| 3,809,086 A | 5/1974 | Schachet et al. | |
| 3,823,720 A | 7/1974 | Tribble | |
| 3,874,387 A | 4/1975 | Barbieri | |
| 3,880,164 A | 4/1975 | Stepno | |
| 3,943,734 A * | 3/1976 | Fleissner | D06B 3/203 |
| | | | 68/5 D |
| 3,980,166 A | 9/1976 | DeFeudis | |
| 4,063,556 A | 12/1977 | Thomas et al. | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,164,027 A | 8/1979 | Bonnie et al. | |
| 4,202,331 A | 5/1980 | Yale | |
| 4,224,945 A | 9/1980 | Cohen | |
| 4,228,798 A | 10/1980 | Deaton | |
| 4,231,357 A | 11/1980 | Hessner | |
| 4,261,363 A | 4/1981 | Russo | |
| 4,266,545 A | 5/1981 | Moss | |
| 4,280,680 A | 7/1981 | Payne | |
| 4,360,015 A | 11/1982 | Mayer | |
| 4,382,441 A | 5/1983 | Svedman | |
| 4,392,853 A | 7/1983 | Muto | |
| 4,422,483 A | 12/1983 | Zins | |
| 4,465,485 A | 8/1984 | Kashmer et al. | |
| 4,468,219 A | 8/1984 | George et al. | |
| 4,499,896 A | 2/1985 | Heinecke | |
| 4,510,802 A | 4/1985 | Peters | |
| 4,524,064 A | 6/1985 | Nambu | |
| 4,538,645 A | 9/1985 | Perach | |
| 4,540,412 A | 9/1985 | Van Overloop | |
| 4,553,967 A | 11/1985 | Ferguson et al. | |
| 4,561,435 A | 12/1985 | McKnight et al. | |
| 4,569,674 A | 2/1986 | Phillips et al. | |
| 4,579,120 A | 4/1986 | MacGregor | |
| 4,600,001 A | 7/1986 | Gilman | |
| 4,605,399 A | 8/1986 | Weston et al. | |
| 4,614,183 A | 9/1986 | McCracken et al. | |
| 4,617,326 A | 10/1986 | Bjornberg et al. | |
| 4,655,754 A | 4/1987 | Richmond et al. | |
| 4,700,479 A | 10/1987 | Saito et al. | |
| 4,710,165 A | 12/1987 | McNeil et al. | |
| 4,738,257 A | 4/1988 | Meyer et al. | |
| 4,743,232 A | 5/1988 | Kruger | |
| 4,786,282 A | 11/1988 | Wagle et al. | |
| 4,826,494 A | 5/1989 | Richmond et al. | |
| 4,870,975 A | 10/1989 | Cronk et al. | |
| 4,874,363 A | 10/1989 | Abell | |
| 4,906,240 A | 3/1990 | Reed et al. | |
| 4,917,112 A | 4/1990 | Kalt | |
| 4,921,492 A | 5/1990 | Schultz et al. | |
| 4,941,882 A | 7/1990 | Ward et al. | |
| 4,969,880 A | 11/1990 | Zamierowski | |
| 4,980,226 A | 12/1990 | Hellgren et al. | |
| 4,984,570 A | 1/1991 | Langen et al. | |
| 4,990,137 A | 2/1991 | Graham | |
| 4,997,438 A | 3/1991 | Nipper | |
| 5,000,172 A | 3/1991 | Ward | |
| 5,009,224 A | 4/1991 | Cole | |
| RE33,727 E | 10/1991 | Sims | |
| 5,053,021 A | 10/1991 | Feibus | |
| 5,056,510 A | 10/1991 | Gilman | |
| 5,059,424 A | 10/1991 | Cartmell et al. | |
| 5,060,642 A | 10/1991 | Gilman | |
| 5,071,409 A | 12/1991 | Rosenberg | |
| 5,088,483 A | 2/1992 | Heinecke | |
| 5,100,395 A | 3/1992 | Rosenberg | |
| 5,100,396 A | 3/1992 | Zamierowski | |
| 5,106,362 A | 4/1992 | Gilman | |
| 5,106,629 A | 4/1992 | Cartmell et al. | |
| 5,112,323 A | 5/1992 | Winkler et al. | |
| 5,134,007 A | 7/1992 | Reising et al. | |
| 5,135,485 A | 8/1992 | Cohen et al. | |
| 5,141,503 A | 8/1992 | Sewell, Jr. | |
| 5,147,698 A | 9/1992 | Cole | |
| 5,149,331 A | 9/1992 | Ferdman et al. | |
| 5,152,757 A | 10/1992 | Eriksson | |
| 5,160,315 A | 11/1992 | Heinecke et al. | |
| 5,160,322 A | 11/1992 | Scheremet et al. | |
| 5,160,334 A | 11/1992 | Billings et al. | |
| 5,176,663 A | 1/1993 | Svedman et al. | |
| 5,178,157 A | 1/1993 | Fanlo | |
| 5,180,375 A | 1/1993 | Feibus | |
| 5,195,977 A | 3/1993 | Pollitt | |
| 5,230,496 A | 7/1993 | Shillington et al. | |
| 5,244,457 A | 9/1993 | Karami et al. | |
| 5,261,893 A | 11/1993 | Zamierowski | |
| 5,263,922 A | 11/1993 | Soya et al. | |
| 5,300,054 A | 4/1994 | Feist et al. | |
| 5,304,161 A | 4/1994 | Noel et al. | |
| 5,308,313 A | 5/1994 | Karami et al. | |
| 5,344,415 A * | 9/1994 | DeBusk | A61M 25/02 |
| | | | 604/304 |
| 5,358,492 A | 10/1994 | Feibus | |
| 5,366,451 A | 11/1994 | Levesque | |
| 5,391,161 A | 2/1995 | Hellgren et al. | |
| 5,415,627 A | 5/1995 | Rasmussen et al. | |
| 5,423,737 A | 6/1995 | Cartmell et al. | |
| 5,437,651 A | 8/1995 | Todd et al. | |
| 5,439,458 A | 8/1995 | Noel et al. | |
| 5,447,492 A | 9/1995 | Cartmell et al. | |
| 5,447,499 A | 9/1995 | Allaire et al. | |
| D364,679 S | 11/1995 | Heaton et al. | |
| 5,477,492 A | 12/1995 | Cartmell et al. | |
| 5,484,427 A | 1/1996 | Gibbons | |
| 5,486,167 A | 1/1996 | Dragoo et al. | |
| 5,489,262 A | 2/1996 | Cartmell et al. | |
| 5,501,661 A | 3/1996 | Cartmell et al. | |
| 5,520,629 A | 5/1996 | Heinecke et al. | |
| 5,525,407 A | 6/1996 | Yang | |
| 5,527,293 A | 6/1996 | Zamierowski | |
| 5,527,923 A | 6/1996 | Klingler et al. | |
| 5,531,855 A | 7/1996 | Heinecke et al. | |
| 5,536,233 A | 7/1996 | Khouri | |
| H1585 H | 8/1996 | Ahr | |
| 5,549,584 A | 8/1996 | Gross | |
| 5,588,958 A | 12/1996 | Cunningham et al. | |
| 5,593,750 A | 1/1997 | Rothrum et al. | |
| 5,599,289 A | 2/1997 | Castellana | |
| 5,605,165 A | 2/1997 | Sessions et al. | |
| 5,613,942 A | 3/1997 | Lucast et al. | |
| 5,618,278 A | 4/1997 | Rothrum | |
| 5,624,374 A | 4/1997 | Von Iderstein | |
| 5,624,423 A | 4/1997 | Anjur et al. | |
| 5,628,724 A | 5/1997 | DeBusk et al. | |
| 5,628,735 A | 5/1997 | Skow | |
| 5,628,739 A | 5/1997 | Hsieh et al. | |
| 5,636,643 A | 6/1997 | Argenta et al. | |
| 5,637,093 A | 6/1997 | Hyman et al. | |
| 5,645,081 A | 7/1997 | Argenta et al. | |
| 5,678,564 A | 10/1997 | Lawrence et al. | |
| 5,695,846 A | 12/1997 | Lange et al. | |
| 5,701,917 A | 12/1997 | Khouri | |
| 5,704,905 A | 1/1998 | Jensen et al. | |
| 5,713,842 A | 2/1998 | Kay | |
| 5,733,305 A | 3/1998 | Fleischmann | |
| 5,738,642 A | 4/1998 | Heinecke et al. | |
| 5,749,842 A | 5/1998 | Cheong et al. | |
| 5,779,657 A | 7/1998 | Daneshvar | |
| 5,795,584 A | 8/1998 | Totakura et al. | |
| 5,797,844 A | 8/1998 | Yoshioka et al. | |
| 5,797,894 A | 8/1998 | Cadieux et al. | |
| 5,817,325 A | 10/1998 | Sawan et al. | |
| 5,840,049 A | 11/1998 | Tumey et al. | |
| 5,891,077 A | 4/1999 | Gilman et al. | |
| 5,894,608 A | 4/1999 | Birbara | |
| 5,911,222 A | 6/1999 | Lawrence et al. | |
| 5,914,282 A | 6/1999 | Dunshee et al. | |
| 5,928,174 A | 7/1999 | Gibbins | |
| 5,931,800 A | 8/1999 | Rasmussen et al. | |
| 5,942,218 A | 8/1999 | Kirschner et al. | |
| 5,944,703 A | 8/1999 | Dixon et al. | |

(56) References Cited

U.S. PATENT DOCUMENTS

| | | |
|---|---|---|
| 5,960,837 A | 10/1999 | Cude |
| 5,973,221 A | 10/1999 | Collyer et al. |
| 6,010,524 A | 1/2000 | Fleischmann |
| 6,043,406 A | 3/2000 | Sessions et al. |
| 6,071,267 A | 6/2000 | Zamierowski |
| 6,093,465 A | 7/2000 | Gilchrist et al. |
| 6,117,111 A | 9/2000 | Fleischmann |
| 6,121,508 A | 9/2000 | Bischof et al. |
| 6,135,116 A | 10/2000 | Vogel et al. |
| D434,150 S | 11/2000 | Turney et al. |
| 6,142,982 A | 11/2000 | Hunt et al. |
| 6,168,800 B1 | 1/2001 | Dobos et al. |
| 6,169,224 B1 | 1/2001 | Heinecke et al. |
| 6,174,306 B1 | 1/2001 | Fleischmann |
| 6,203,563 B1 | 3/2001 | Fernandez |
| 6,218,009 B1 | 4/2001 | Tsai et al. |
| 6,261,276 B1 | 7/2001 | Reitsma |
| 6,264,976 B1 | 7/2001 | Heinecke et al. |
| 6,265,605 B1 | 7/2001 | Johnson |
| 6,291,050 B1 | 9/2001 | Cree et al. |
| 6,325,788 B1 | 12/2001 | McKay |
| 6,345,623 B1 | 2/2002 | Heaton et al. |
| 6,348,423 B1 | 2/2002 | Griffiths et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,436,432 B2 | 8/2002 | Heinecke et al. |
| 6,458,109 B1 | 10/2002 | Henley et al. |
| 6,461,467 B2 | 10/2002 | Blatchford et al. |
| 6,479,073 B1 | 11/2002 | Lucast et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| 6,565,544 B1 | 5/2003 | Rainin |
| 6,566,575 B1 | 5/2003 | Stickels et al. |
| D478,659 S | 8/2003 | Hall et al. |
| 6,605,068 B2 | 8/2003 | Righetti |
| 6,607,495 B1 | 8/2003 | Skalak |
| 6,607,799 B1 | 8/2003 | Heinecke et al. |
| 6,622,728 B2 | 9/2003 | Rusin |
| 6,626,891 B2 | 9/2003 | Ohmstede |
| 6,648,862 B2 | 11/2003 | Watson |
| 6,685,681 B2 | 2/2004 | Lockwood et al. |
| 6,685,682 B1 | 2/2004 | Heinecke et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,459 B1 | 7/2004 | Donaldson |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,867,342 B2 | 3/2005 | Johnston et al. |
| 6,878,857 B1 | 4/2005 | Chihani et al. |
| 6,887,228 B2 | 5/2005 | McKay |
| 6,887,263 B2 | 5/2005 | Bleam et al. |
| 6,903,243 B1 | 6/2005 | Burton |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| D515,701 S | 2/2006 | Horhota et al. |
| 6,994,702 B1 | 2/2006 | Johnson |
| 6,994,904 B2 | 2/2006 | Joseph et al. |
| 7,004,915 B2 | 2/2006 | Boynton et al. |
| 7,005,143 B2 | 2/2006 | Abuelyaman et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,580 B2 | 7/2006 | Nielsen |
| 7,070,584 B2 | 7/2006 | Johnson et al. |
| 7,077,832 B2 | 7/2006 | Fleischmann |
| 7,093,600 B2 | 8/2006 | Sorribes |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hanningan et al. |
| 7,169,151 B1 | 1/2007 | Lytinas |
| 7,182,758 B2 | 2/2007 | McCraw |
| 7,183,454 B1 | 2/2007 | Rosenberg |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,276,247 B2 | 10/2007 | Fansler et al. |
| 7,279,612 B1 | 10/2007 | Heaton et al. |
| 7,285,576 B2 | 10/2007 | Hyde et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,442,849 B2 | 10/2008 | Heinecke |
| 7,485,112 B2 | 2/2009 | Karpowicz et al. |
| 7,503,910 B2 | 3/2009 | Adahan |
| 7,531,711 B2 | 5/2009 | Sigurjonsson et al. |
| 7,534,927 B2 | 5/2009 | Lockwood et al. |
| 7,569,742 B2 | 8/2009 | Haggstrom et al. |
| 7,584,860 B2 | 9/2009 | Olson |
| 7,585,554 B2 | 9/2009 | Johnson et al. |
| 7,586,019 B2 | 9/2009 | Oelund et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,700,819 B2 | 4/2010 | Ambrosio et al. |
| 7,723,560 B2 | 5/2010 | Lockwood et al. |
| 7,745,681 B1 | 6/2010 | Ferguson |
| 7,754,937 B2 | 7/2010 | Boehringer et al. |
| 7,758,554 B2 | 7/2010 | Lina et al. |
| 7,759,537 B2 | 7/2010 | Bishop et al. |
| 7,759,539 B2 | 7/2010 | Shaw et al. |
| 7,763,769 B2 | 7/2010 | Johnson et al. |
| 7,779,625 B2 | 8/2010 | Joshi et al. |
| 7,781,639 B2 | 8/2010 | Johnston et al. |
| 7,790,945 B1 | 9/2010 | Watson, Jr. et al. |
| 7,790,946 B2 | 9/2010 | Mulligan |
| 7,794,438 B2 | 9/2010 | Henley et al. |
| 7,815,616 B2 | 10/2010 | Boehringer et al. |
| 7,846,141 B2 | 12/2010 | Weston |
| 7,862,718 B2 | 1/2011 | Doyen et al. |
| 7,880,050 B2 | 2/2011 | Robinson et al. |
| 7,888,546 B2 | 2/2011 | Marcoux et al. |

(56) References Cited

U.S. PATENT DOCUMENTS

| | | |
|---|---|---|
| 7,896,856 B2 | 3/2011 | Petrosenko et al. |
| 7,896,864 B2 | 3/2011 | Lockwood et al. |
| 7,909,805 B2 | 3/2011 | Weston |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,533 B2 | 7/2011 | Larsson |
| 7,981,098 B2 | 7/2011 | Boehringer et al. |
| 7,981,136 B2 | 7/2011 | Weiser |
| 8,002,313 B2 | 8/2011 | Singh et al. |
| 8,021,347 B2 | 9/2011 | Vitaris et al. |
| 8,030,534 B2 | 10/2011 | Radl et al. |
| 8,057,449 B2 | 11/2011 | Sanders et al. |
| 8,062,272 B2 | 11/2011 | Weston |
| 8,079,991 B2 | 12/2011 | Watson |
| 8,083,712 B2 | 12/2011 | Biggie et al. |
| 8,084,663 B2 | 12/2011 | Watson, Jr. |
| 8,133,211 B2 | 3/2012 | Cavanaugh, II et al. |
| 8,142,419 B2 | 3/2012 | Heaton et al. |
| 8,147,468 B2 | 4/2012 | Barta et al. |
| 8,148,595 B2 | 4/2012 | Robinson et al. |
| 8,152,785 B2 | 4/2012 | Vitaris |
| 8,158,844 B2 | 4/2012 | McNeil |
| 8,162,907 B2 | 4/2012 | Heagle |
| 8,187,237 B2 | 5/2012 | Seegert |
| 8,188,331 B2 | 5/2012 | Barta et al. |
| 8,202,261 B2 | 6/2012 | Kazala, Jr. et al. |
| 8,241,261 B2 | 8/2012 | Randolph et al. |
| 8,257,326 B2 | 9/2012 | Vitaris |
| 8,257,327 B2 | 9/2012 | Blott et al. |
| 8,298,200 B2 | 10/2012 | Vess et al. |
| 8,376,972 B2 | 2/2013 | Fleischmann |
| 8,382,731 B2 | 2/2013 | Johannison |
| 8,409,170 B2 * | 4/2013 | Locke ................ A61M 1/0031 604/540 |
| 8,469,915 B2 | 6/2013 | Johannison et al. |
| 8,491,548 B2 | 7/2013 | Livne et al. |
| 8,545,466 B2 | 10/2013 | Andresen et al. |
| 8,641,691 B2 | 2/2014 | Fink et al. |
| 8,734,410 B2 | 5/2014 | Hall et al. |
| 8,784,392 B2 | 7/2014 | Vess et al. |
| 9,017,302 B2 | 4/2015 | Vitaris et al. |
| 9,033,942 B2 | 5/2015 | Vess |
| 9,227,000 B2 | 1/2016 | Fink et al. |
| 9,474,654 B2 | 10/2016 | Heagle et al. |
| 2001/0020145 A1 | 9/2001 | Satterfield |
| 2001/0031943 A1 | 10/2001 | Urie |
| 2001/0034223 A1 | 10/2001 | Rieser et al. |
| 2001/0043943 A1 | 11/2001 | Coffey |
| 2002/0002209 A1 | 1/2002 | Mork |
| 2002/0016577 A1 | 2/2002 | Ohmstede |
| 2002/0108614 A1 | 8/2002 | Schultz |
| 2002/0115952 A1 | 8/2002 | Johnson et al. |
| 2002/0115967 A1 | 8/2002 | Svedman |
| 2002/0128578 A1 | 9/2002 | Johnson |
| 2002/0143286 A1 | 10/2002 | Tumey |
| 2002/0151836 A1 | 10/2002 | Burden |
| 2002/0161346 A1 | 10/2002 | Lockwood et al. |
| 2002/0182246 A1 | 12/2002 | Oyaski |
| 2003/0078532 A1 | 4/2003 | Ruszczak et al. |
| 2003/0087568 A1 | 5/2003 | Kinn et al. |
| 2003/0093041 A1 | 5/2003 | Risk, Jr. et al. |
| 2003/0170453 A1 | 9/2003 | Foss et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0082925 A1 | 4/2004 | Patel |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0214495 A1 | 10/2004 | Foss et al. |
| 2004/0241213 A1 | 12/2004 | Bray |
| 2004/0241216 A1 | 12/2004 | Klun et al. |
| 2004/0243073 A1 | 12/2004 | Lockwood et al. |
| 2004/0249353 A1 | 12/2004 | Risks, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0065484 A1 | 3/2005 | Watson, Jr. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0165445 A1 * | 7/2005 | Buckman ................ A61F 13/00 606/213 |
| 2005/0177190 A1 | 8/2005 | Zamierowski |
| 2005/0182445 A1 | 8/2005 | Zamierowski |
| 2005/0203452 A1 | 9/2005 | Weston et al. |
| 2005/0222527 A1 | 10/2005 | Miller et al. |
| 2005/0261643 A1 | 11/2005 | Bybordi et al. |
| 2005/0273066 A1 | 12/2005 | Wittmann |
| 2005/0288691 A1 | 12/2005 | Leiboff |
| 2006/0009744 A1 | 1/2006 | Erdman et al. |
| 2006/0015087 A1 | 1/2006 | Risk, Jr. et al. |
| 2006/0029650 A1 | 2/2006 | Coffey |
| 2006/0036221 A1 | 2/2006 | Watson, Jr. |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0127462 A1 | 6/2006 | Canada et al. |
| 2006/0129080 A1 | 6/2006 | Bjornberg et al. |
| 2006/0148349 A1 | 7/2006 | Naor et al. |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0038172 A1 | 2/2007 | Zamierowski |
| 2007/0055209 A1 | 3/2007 | Patel et al. |
| 2007/0078432 A1 | 4/2007 | Halseth et al. |
| 2007/0156104 A1 | 7/2007 | Lockwood et al. |
| 2007/0167927 A1 | 7/2007 | Hunt et al. |
| 2007/0179460 A1 | 8/2007 | Adahan |
| 2007/0219497 A1 | 9/2007 | Johnson et al. |
| 2007/0219513 A1 | 9/2007 | Lina |
| 2007/0219516 A1 | 9/2007 | Patel et al. |
| 2007/0219532 A1 | 9/2007 | Karpowicz et al. |
| 2007/0225663 A1 | 9/2007 | Watt et al. |
| 2007/0233022 A1 | 10/2007 | Henley et al. |
| 2007/0265585 A1 | 11/2007 | Joshi et al. |
| 2007/0282310 A1 * | 12/2007 | Bengtson ............ A61M 1/0088 604/543 |
| 2008/0011667 A1 | 1/2008 | Ruschke |
| 2008/0033325 A1 | 2/2008 | Van der Hulst |
| 2008/0033401 A1 | 2/2008 | Watson |
| 2008/0051688 A1 | 2/2008 | Lowe |
| 2008/0071235 A1 | 3/2008 | Locke et al. |
| 2008/0103462 A1 | 5/2008 | Wenzel et al. |
| 2008/0103489 A1 | 5/2008 | Dahners |
| 2008/0108977 A1 | 5/2008 | Heaton et al. |
| 2008/0119802 A1 | 5/2008 | Reisinger |

(56) References Cited

U.S. PATENT DOCUMENTS

| | | |
|---|---|---|
| 2008/0132819 A1 | 6/2008 | Radl et al. |
| 2008/0161778 A1 | 7/2008 | Steward |
| 2008/0167593 A1 | 7/2008 | Flesichmann |
| 2008/0177253 A1* | 7/2008 | Boehringer ....... A61F 13/00021 604/543 |
| 2008/0183233 A1 | 7/2008 | Koch et al. |
| 2008/0195017 A1 | 8/2008 | Robinson et al. |
| 2008/0199536 A1 | 8/2008 | Terry |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0243096 A1 | 10/2008 | Svedman |
| 2008/0281281 A1 | 11/2008 | Meyer et al. |
| 2008/0300578 A1 | 12/2008 | Freedman |
| 2008/0306456 A1 | 12/2008 | Riesinger |
| 2009/0005744 A1 | 1/2009 | Karpowicz et al. |
| 2009/0012501 A1 | 1/2009 | Boehringer et al. |
| 2009/0093778 A1 | 4/2009 | Svedman |
| 2009/0099519 A1 | 4/2009 | Kaplan |
| 2009/0105670 A1 | 4/2009 | Bentley et al. |
| 2009/0124988 A1 | 5/2009 | Coulthard |
| 2009/0131892 A1 | 5/2009 | Karpowicz et al. |
| 2009/0137973 A1 | 5/2009 | Karpowicz et al. |
| 2009/0157016 A1 | 6/2009 | Adahan |
| 2009/0171288 A1 | 7/2009 | Wheeler |
| 2009/0192467 A1 | 7/2009 | Hansen et al. |
| 2009/0192499 A1 | 7/2009 | Weston et al. |
| 2009/0227968 A1 | 9/2009 | Vess |
| 2009/0227969 A1 | 9/2009 | Jaeb et al. |
| 2009/0234307 A1 | 9/2009 | Vitaris |
| 2009/0234313 A1 | 9/2009 | Mullejeans et al. |
| 2009/0264805 A1 | 10/2009 | Davis et al. |
| 2009/0264837 A1 | 10/2009 | Adahan |
| 2009/0281526 A1 | 11/2009 | Kenny et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299303 A1 | 12/2009 | Seegert |
| 2009/0299307 A1 | 12/2009 | Barta et al. |
| 2009/0299308 A1 | 12/2009 | Kazala et al. |
| 2009/0299340 A1 | 12/2009 | Kazala et al. |
| 2009/0299341 A1 | 12/2009 | Kazala et al. |
| 2009/0299342 A1 | 12/2009 | Cavanaugh, II et al. |
| 2009/0312728 A1 | 12/2009 | Randolph et al. |
| 2010/0000524 A1 | 1/2010 | Ohbi |
| 2010/0010458 A1 | 1/2010 | Sherman |
| 2010/0016767 A1 | 1/2010 | Jones et al. |
| 2010/0016815 A1 | 1/2010 | Vitaris et al. |
| 2010/0028390 A1 | 2/2010 | Cleary et al. |
| 2010/0036334 A1 | 2/2010 | Heagle et al. |
| 2010/0069850 A1 | 3/2010 | Fabo |
| 2010/0069858 A1 | 3/2010 | Olson |
| 2010/0069863 A1 | 3/2010 | Olson |
| 2010/0069885 A1 | 3/2010 | Stevenson et al. |
| 2010/0069886 A1 | 3/2010 | Wilkes |
| 2010/0087767 A1* | 4/2010 | McNeil ............... A61M 1/0088 602/42 |
| 2010/0094234 A1 | 4/2010 | Ramella et al. |
| 2010/0106106 A1 | 4/2010 | Heaton et al. |
| 2010/0106188 A1 | 4/2010 | Heaton et al. |
| 2010/0125258 A1 | 5/2010 | Coulthard et al. |
| 2010/0152639 A1 | 6/2010 | Miau et al. |
| 2010/0160853 A1 | 6/2010 | Smith et al. |
| 2010/0160878 A1 | 6/2010 | Hunt et al. |
| 2010/0160901 A1 | 6/2010 | Hu et al. |
| 2010/0185163 A1 | 7/2010 | Heagle |
| 2010/0191198 A1 | 7/2010 | Heagle |
| 2010/0210986 A1 | 8/2010 | Sanders |
| 2010/0224540 A1 | 9/2010 | Rolchigo et al. |
| 2010/0262091 A1 | 10/2010 | Larsson |
| 2010/0262095 A1 | 10/2010 | Hall et al. |
| 2010/0268128 A1 | 10/2010 | Randolph |
| 2010/0286635 A1 | 11/2010 | Watson, Jr. |
| 2010/0305524 A1 | 12/2010 | Vess et al. |
| 2010/0324510 A1 | 12/2010 | Andresen et al. |
| 2010/0324516 A1 | 12/2010 | Braga et al. |
| 2011/0015556 A1 | 1/2011 | Fabo et al. |
| 2011/0028290 A1 | 2/2011 | Ozawa |
| 2011/0028919 A1 | 2/2011 | Johnnison et al. |
| 2011/0028920 A1 | 2/2011 | Johannison |
| 2011/0125066 A1 | 5/2011 | Robinson et al. |
| 2011/0125110 A1 | 5/2011 | Cotton |
| 2011/0130712 A1 | 6/2011 | Topaz |
| 2011/0230849 A1 | 9/2011 | Coulthard et al. |
| 2012/0143156 A1 | 6/2012 | Bannister et al. |
| 2012/0253255 A1 | 10/2012 | Tsuruta et al. |
| 2012/0302976 A1 | 11/2012 | Locke et al. |
| 2014/0163486 A1 | 6/2014 | Riesinger |
| 2015/0073358 A1 | 3/2015 | Jaeb et al. |

FOREIGN PATENT DOCUMENTS

| | | |
|---|---|---|
| DE | 41 11 122 A1 | 4/1993 |
| DE | 43 06 478 | 9/1994 |
| DE | 295 04 378 U1 | 10/1995 |
| DE | 20 2010 009 1 | 10/2010 |
| EP | 0 358 302 | 3/1990 |
| EP | 0 325 771 B1 | 9/1993 |
| EP | 0 392 640 B1 | 6/1995 |
| EP | 0 441 418 B1 | 7/1995 |
| EP | 0 688 189 B2 | 12/1995 |
| EP | 0 465 601 B1 | 1/1997 |
| EP | 0 751 757 B1 | 1/1997 |
| EP | 0 692 987 B1 | 10/1997 |
| EP | 0 853 950 | 7/1998 |
| EP | 0 651 983 B1 | 9/1998 |
| EP | 0 777 504 B1 | 10/1998 |
| EP | 0 782 421 B1 | 7/1999 |
| EP | 0 690 706 B1 | 11/2000 |
| EP | 0 865 304 | 7/2001 |
| EP | 1 129 734 A2 | 9/2001 |
| EP | 0 921 775 B1 | 12/2001 |
| EP | 1 169 071 A1 | 1/2002 |
| EP | 1 219 311 | 7/2002 |
| EP | 1 897 569 | 8/2002 |
| EP | 1 283 702 A1 | 2/2003 |
| EP | 0 708 620 B1 | 5/2003 |
| EP | 1 014 905 B1 | 5/2003 |
| EP | 1 088 569 | 8/2003 |
| EP | 0 993 317 B1 | 9/2003 |
| EP | 0 880 953 B1 | 10/2003 |
| EP | 1 440 667 | 7/2004 |
| EP | 1 018 967 | 8/2004 |
| EP | 1 448 261 A1 | 8/2004 |
| EP | 1 478 313 A2 | 11/2004 |
| EP | 1 487 389 | 12/2004 |
| EP | 1 100 574 B1 | 2/2005 |
| EP | 1 513 478 A2 | 3/2005 |
| EP | 1 517 660 A2 | 3/2005 |
| EP | 1 556 120 A2 | 7/2005 |
| EP | 1 565 219 A2 | 8/2005 |
| EP | 1 440 667 | 3/2006 |
| EP | 1 637 088 A2 | 3/2006 |
| EP | 1 284 777 B1 | 4/2006 |
| EP | 1 663 062 A2 | 6/2006 |
| EP | 0 982 015 B1 | 8/2006 |
| EP | 0 620 720 B2 | 11/2006 |
| EP | 1 448 261 | 2/2007 |
| EP | 1 171 065 | 3/2007 |
| EP | 1 772 160 A1 | 4/2007 |
| EP | 1 809 350 | 7/2007 |
| EP | 1 824 533 A2 | 8/2007 |
| EP | 1 227 853 B1 | 1/2008 |
| EP | 1 476 217 B1 | 3/2008 |
| EP | 1 904 137 | 4/2008 |
| EP | 1 909 863 A1 | 4/2008 |
| EP | 2 218 431 A2 | 4/2008 |
| EP | 1906903 A2 | 4/2008 |
| EP | 1 919 533 | 5/2008 |
| EP | 1 920 791 A2 | 5/2008 |

(56) References Cited

FOREIGN PATENT DOCUMENTS

| | | |
|---|---|---|
| EP | 1 931 413 | 6/2008 |
| EP | 1 233 808 B1 | 7/2008 |
| EP | 1 940 485 A2 | 7/2008 |
| EP | 1 957 018 A2 | 8/2008 |
| EP | 1 976 477 A2 | 10/2008 |
| EP | 1 977 776 | 10/2008 |
| EP | 1 977 776 A2 | 10/2008 |
| EP | 1 986 584 A2 | 11/2008 |
| EP | 1 986 718 | 11/2008 |
| EP | 1 993 652 | 11/2008 |
| EP | 1 993 653 | 11/2008 |
| EP | 1993491 A2 | 11/2008 |
| EP | 1 807 184 | 12/2008 |
| EP | 1 827 561 B1 | 1/2009 |
| EP | 2 010 065 A1 | 1/2009 |
| EP | 2 037 852 | 3/2009 |
| EP | 2 052 750 A1 | 4/2009 |
| EP | 2 063 952 A1 | 6/2009 |
| EP | 2 068 798 | 6/2009 |
| EP | 2 079 507 | 7/2009 |
| EP | 2 081 629 A2 | 7/2009 |
| EP | 1 496 822 | 8/2009 |
| EP | 2 098 257 A1 | 9/2009 |
| EP | 2 103 290 A2 | 9/2009 |
| EP | 2 109 427 | 10/2009 |
| EP | 2 109 473 | 10/2009 |
| EP | 2 346 561 | 11/2009 |
| EP | 1 513 478 B1 | 12/2009 |
| EP | 2 129 409 A1 | 12/2009 |
| EP | 2 138 139 A2 | 12/2009 |
| EP | 1 652 549 B1 | 1/2010 |
| EP | 1 905 465 B1 | 1/2010 |
| EP | 2 146 759 A1 | 1/2010 |
| EP | 2 152 196 A1 | 2/2010 |
| EP | 2 127 690 A2 | 3/2010 |
| EP | 2 167 157 A1 | 3/2010 |
| EP | 2 172 164 | 4/2010 |
| EP | 2 195 069 | 6/2010 |
| EP | 2 203 137 A1 | 7/2010 |
| EP | 2 244 217 A1 | 10/2010 |
| EP | 2 244 746 A2 | 11/2010 |
| EP | 2 252 247 A2 | 11/2010 |
| EP | 2 254 537 A2 | 12/2010 |
| EP | 2 268 348 | 1/2011 |
| EP | 2 274 025 | 1/2011 |
| EP | 2 279 017 A1 | 2/2011 |
| EP | 2 279 018 A1 | 2/2011 |
| EP | 2 285 430 A2 | 2/2011 |
| EP | 2 296 723 | 3/2011 |
| EP | 2 306 951 A1 | 4/2011 |
| EP | 1 703 922 B1 | 5/2011 |
| EP | 2 319 550 | 5/2011 |
| EP | 2 334 349 | 6/2011 |
| EP | 2 340 064 | 7/2011 |
| EP | 2 344 217 | 7/2011 |
| EP | 2 346 468 | 7/2011 |
| EP | 1 578 477 B1 | 9/2011 |
| EP | 2 370 116 | 10/2011 |
| EP | 1 169 071 | 2/2012 |
| EP | 2 413 858 | 2/2012 |
| EP | 2 435 000 | 4/2012 |
| EP | 1 660 000 | 10/2012 |
| EP | 2 545 946 | 3/2013 |
| EP | 2 279 017 | 8/2013 |
| EP | 2 659 915 | 11/2013 |
| EP | 1 339 366 | 6/2014 |
| EP | 2 051 675 | 6/2014 |
| EP | 1 478 313 | 8/2014 |
| EP | 2 146 759 | 9/2014 |
| GB | 488 232 | 7/1938 |
| GB | 1 415 096 | 11/1975 |
| GB | 1 549 756 | 8/1979 |
| GB | 2 195 255 A | 4/1988 |
| GB | 2 235 877 A | 3/1991 |
| GB | 2 307 180 A | 11/1996 |
| GB | 2 329 127 A | 3/1999 |
| GB | 2 336 546 A | 10/1999 |
| GB | 2 307 180 B | 6/2000 |
| GB | 2 344 531 A | 6/2000 |
| GB | 2 356 148 B2 | 6/2004 |
| GB | 2 415 908 | 1/2006 |
| GB | 2 431 351 A1 | 4/2007 |
| SU | 1762940 | 1/1989 |
| WO | WO 1980/01139 | 6/1980 |
| WO | WO 1980/02182 | 10/1980 |
| WO | WO 1984/01904 | 5/1984 |
| WO | WO 1989/05133 | 6/1989 |
| WO | WO 1990/11795 | 10/1990 |
| WO | WO 1992/19313 | 11/1992 |
| WO | WO 1993/009727 | 5/1993 |
| WO | WO 1994/03214 | 2/1994 |
| WO | WO 1994/20041 | 9/1994 |
| WO | WO 1994/21207 | 9/1994 |
| WO | WO 1994/23678 | 10/1994 |
| WO | WO 1995/025492 | 9/1995 |
| WO | WO 1996/05873 | 2/1996 |
| WO | WO 1999/01173 | 1/1999 |
| WO | WO 2000/07653 | 2/2000 |
| WO | WO 2000/21586 | 4/2000 |
| WO | WO 2000/61206 | 10/2000 |
| WO | WO 2001/85228 | 11/2001 |
| WO | WO 2001/85248 | 11/2001 |
| WO | WO 2002/043634 | 6/2002 |
| WO | WO 2002/070040 | 9/2002 |
| WO | WO 2003/005943 | 1/2003 |
| WO | WO 2003/018098 | 3/2003 |
| WO | WO 2003/030966 | 4/2003 |
| WO | WO 2003/045492 | 6/2003 |
| WO | WO 2003/057070 | 7/2003 |
| WO | WO 2003/057071 | 7/2003 |
| WO | WO 2003/057307 | 7/2003 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2004/037334 | 5/2004 |
| WO | WO 2004/041064 | 5/2004 |
| WO | WO 2004/060148 | 7/2004 |
| WO | WO 2005/009488 | 2/2005 |
| WO | WO 2005/016179 | 2/2005 |
| WO | WO 2005/025447 | 3/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/061025 | 7/2005 |
| WO | WO 2005/072789 | 8/2005 |
| WO | WO 2005/079718 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105179 | 11/2005 |
| WO | WO 2005/105180 | 11/2005 |
| WO | WO 2005/115497 | 12/2005 |
| WO | WO 2005/115523 | 12/2005 |
| WO | WO 2005/123170 | 12/2005 |
| WO | WO 2006/015599 | 2/2006 |
| WO | WO 2006/046060 | 5/2006 |
| WO | WO 2006/052338 | 5/2006 |
| WO | WO 2006/052745 | 5/2006 |
| WO | WO 2006/105892 | 10/2006 |
| WO | WO 2006/114637 | 11/2006 |
| WO | WO 2006/114638 | 11/2006 |
| WO | WO 2006/114648 | 11/2006 |
| WO | WO 2007/006306 | 1/2007 |
| WO | WO 2007/013049 | 2/2007 |
| WO | WO 2007/013064 | 2/2007 |
| WO | WO 2007/015964 | 2/2007 |
| WO | WO 2007/016590 | 2/2007 |
| WO | WO 2007/019038 | 2/2007 |
| WO | WO 2007/030598 | 3/2007 |
| WO | WO 2007/030599 | 3/2007 |
| WO | WO 2007/030601 A2 | 3/2007 |

(56) References Cited

FOREIGN PATENT DOCUMENTS

| | | |
|---|---|---|
| WO | WO 2007/030601 A3 | 3/2007 |
| WO | WO 2007/031757 | 3/2007 |
| WO | WO 2007/031762 | 3/2007 |
| WO | WO 2007/031765 | 3/2007 |
| WO | WO 2007/041642 | 4/2007 |
| WO | WO 2007/062024 | 5/2007 |
| WO | WO 2007/067685 | 6/2007 |
| WO | WO 2007/085396 | 8/2007 |
| WO | WO 2007/087808 | 8/2007 |
| WO | WO 2007/087809 | 8/2007 |
| WO | WO 2007/087811 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/133618 | 11/2007 |
| WO | WO 2007/143060 | 12/2007 |
| WO | WO 2008/008032 | 1/2008 |
| WO | WO 2008/010094 | 1/2008 |
| WO | WO 2008/011774 | 1/2008 |
| WO | WO 2008/012278 | 1/2008 |
| WO | WO 2008/013896 | 1/2008 |
| WO | WO 2008/014358 | 1/2008 |
| WO | WO 2008/016304 | 2/2008 |
| WO | WO 2008/020862 | 2/2008 |
| WO | WO 2008/027449 | 3/2008 |
| WO | WO 2008/036162 | 3/2008 |
| WO | WO 2008/040020 | 4/2008 |
| WO | WO 2008/041926 | 4/2008 |
| WO | WO 2008/043067 | 4/2008 |
| WO | WO 2008/048481 | 4/2008 |
| WO | WO 2008/048527 | 4/2008 |
| WO | WO 2008/064502 | 6/2008 |
| WO | WO 2008/086397 | 7/2008 |
| WO | WO 2008/100437 | 8/2008 |
| WO | WO 2008/100440 | 8/2008 |
| WO | WO 2008/100446 | 8/2008 |
| WO | WO 2008/112304 | 9/2008 |
| WO | WO 2008/131895 | 11/2008 |
| WO | WO 2008/132215 | 11/2008 |
| WO | WO 2008/135997 | 11/2008 |
| WO | WO 2008/141470 | 11/2008 |
| WO | WO 2008/154158 | 12/2008 |
| WO | WO 2009/002260 | 12/2008 |
| WO | WO-2009002260 A1 * 12/2008 | .......... A61M 1/0088 |
| WO | WO 2009/004370 | 1/2009 |
| WO | WO 2009/016603 | 2/2009 |
| WO | WO 2009/016605 | 2/2009 |
| WO | WO 2009/019229 | 2/2009 |
| WO | WO 2009/021047 | 2/2009 |
| WO | WO 2009/021353 | 2/2009 |
| WO | WO 2009/034322 | 3/2009 |
| WO | WO 2009/062327 | 5/2009 |
| WO | WO 2009/066104 | 5/2009 |
| WO | WO 2009/066106 | 5/2009 |
| WO | WO 2009/067711 | 5/2009 |
| WO | WO 2009/068665 | 6/2009 |
| WO | WO 2009/071926 | 6/2009 |
| WO | WO 2009/071929 | 6/2009 |
| WO | WO 2009/071932 | 6/2009 |
| WO | WO 2009/071933 | 6/2009 |
| WO | WO 2009/071935 | 6/2009 |
| WO | WO 2009/071948 | 6/2009 |
| WO | WO 2009/078790 | 6/2009 |
| WO | WO 2009/086580 | 7/2009 |
| WO | WO 2009/088925 | 7/2009 |
| WO | WO 2009/111655 | 9/2009 |
| WO | WO 2009/114624 | 9/2009 |
| WO | WO 2009/114760 | 9/2009 |
| WO | WO 2009/114790 | 9/2009 |
| WO | WO 2009/124473 | 10/2009 |
| WO | WO 2009/124548 | 10/2009 |
| WO | WO 2009/126102 | 10/2009 |
| WO | WO 2009/126103 | 10/2009 |
| WO | WO 2009/137194 | 11/2009 |
| WO | WO 2009/140376 | 11/2009 |
| WO | WO 2009/141820 | 11/2009 |
| WO | WO 2009/145703 | 12/2009 |
| WO | WO 2009/145894 | 12/2009 |
| WO | WO 2009/158125 | 12/2009 |
| WO | WO 2009/158126 | 12/2009 |
| WO | WO 2009/158127 | 12/2009 |
| WO | WO 2009/158129 | 12/2009 |
| WO | WO 2010/014177 | 2/2010 |
| WO | WO 2010/033271 | 3/2010 |
| WO | WO 2010/033272 | 3/2010 |
| WO | WO 2010/033574 | 3/2010 |
| WO | WO 2010/033769 | 3/2010 |
| WO | WO 2010/035017 | 4/2010 |
| WO | WO 2010/042240 | 4/2010 |
| WO | WO 2010/051073 | 5/2010 |
| WO | WO 2010/056977 | 5/2010 |
| WO | WO 2010/059712 | 5/2010 |
| WO | WO 2010/059730 | 5/2010 |
| WO | WO 2010/072395 | 7/2010 |
| WO | WO 2010/078166 | 7/2010 |
| WO | WO 2010/085270 A1 | 7/2010 |
| WO | WO 2010/094957 A1 | 8/2010 |
| WO | WO 2010/147533 | 12/2010 |
| WO | WO 2010/147592 | 12/2010 |
| WO | WO 2011/049562 | 4/2011 |
| WO | WO 2011/100851 | 8/2011 |
| WO | WO 2011/115908 | 9/2011 |
| WO | WO 2012/142002 | 10/2012 |
| WO | WO 2012/166428 | 12/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2015/018720 | 2/2015 |

OTHER PUBLICATIONS

U.S. Appl. No. 14/261,296, filed Apr. 24, 2014, Heagle et al.
U.S. Appl. No. 14/696,211, filed Apr. 24, 2015, Vitaris et al.
Canadian Office Action, re CA Application No. 2,765,455 dated Feb. 12, 2013.
Fleischmann, W. et al., "Vacuum Sealing: Indication, Technique and Results", Emr J Orthop Surg Tramatol (1995) 5:37-40.
International Search Report and Written Opinion, re PCT Application No. PCT/US2009/047877, dated Aug. 17, 2009.
International Preliminary Report on Patentability, re PCT Application No. PCT/US2009/047877, dated Jan. 5, 2012.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bier, A., Hyperemia as a Therapeutic Agent, Ed. Dr. Gustavus M. Blech, A. Robertson & Co., Chicago 1905.
Arnljots, et al., "Irrigation Treatment in Split-thickness Skin Grafting of Intractable Leg Ulcers," Scand J Plast Reconstr Surg 19: 211-213,1985.
Chardack et al., "Experimental Studies on Synthetic Substitutes for Skin and Their Use in the Treatment of Burns," vol. 155, No. 1 (128-136), 1961.
Chariker, M.E., et al, "Effective Management of Incisional and Cutaneous Fistulae with Closed Suction Wound Drainage," Contemporary Surgery. Jun. 1989, pp. 59-63, vol. 34.
Fleischmann, "Vacuum Sealing for Treatment of Problematical Wounds", University Surgical Clinic and Polyclinic-Accident Surgery Department, WundForum Spezial-IHW, 1994.
Gorica Zivadinovic, et al., "Vacuum Therapy in the Treatment of Peripheral Blood Vessels," Conference Papers of the 5th Timok Medical Days, Majdanpek, 1986 (161-164).
Greer, et al., Techniques for Applying Subatmospheric Pressure Dressing to Wounds in Difficult Regions of Anatomy, JWOCN, vol. 26, No. 5, 1999 pp. 250-253.
Jeter, Katherine F., et al., "Managing Draining Wounds and Fistulae: New and Established Methods", Chronic Wound Care, 1990, pp. 240-246.

(56) References Cited

OTHER PUBLICATIONS

Kampf, Gunter et al., "Microbicidal Activity of a New Silver-Containing Polymer," SPI-Argent II. Sep. 1998, Antimicrobial Agents and Chemotherapy, p. 2440-2442.

KCI, Inc., Basic Application Guide for V.A.C. Dressings for Wounds Without Exposed Vessels, Organs, Tendons and Nerves, 2008, in 2 pages.

KCI, Inc., V.A.C. Abdominal Dressing System: An Advanced Dressing for Managing the Open Abdomen, 2006, in 6 pages.

KCI, Inc., V.A.C. Therapy Clinical Guidelines, A reference source for clinicians, Jul. 2007, in 92 pages.

Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.

Meyer, MD., et al., "In Surgery, Medicine and the Specialties A Manual of its Practical Application", Bier's Hyperemic Treatment, Second Revised Edition, W.B. Saunders Company, 1909.

Mulder, GD, et al., "Clinicians' Pocket Guide to Chronic Wound Repair," Wound Healing Publications Second Edition, 1991.

Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (322-326).

Sandén, Göran MD., et al., "Staphylococcal Wound Infection in the Pig: Part II. Inoculation, Quantification of Bacteria, and Reproducibility," Annals of Plastic Surgery, vol. 23, No. 3, Sep. 1989, (219-223).

Stoll, "Energetic Remedies—Cupping: Healing Within a Vacuum," https://www.suite101.com/article.cfm/ energetic)remedies/74531, Apr. 13, 2005.

Svedman, "A Dressing Allowing Continuous Treatment of a Biosurface," IRCS Medical Science: Biomedical Technology; Clinical Medicine; Surgery and Transplantation, 7, 221 (1979).

Svedman, "A Dressing System Providing Fluid Supply and Suction Drainage Used for Continuous or Intermittent Irrigation," Annals of Plastic Surgery, vol. 17, No. 2, Aug. 1986 (125-133).

Svedman, P., "Irrigation Treatment of Leg Ulcers," The Lancet, Sep. 3, 1983 (532-534).

Svedman, et al., "*Staphylococcal* Wound Infection in the Pig: Part I. Course," Annals of Plastic Surgery, vol. 23, No. 3, Sep. 1989 (212-218).

Teder et al., "Continuous Wound Irrigation in the Pig," Journal of Investigative Surgery, 1990, vol. 3, pp. 399-407.

Usupov, et al., "Active Wound Drainage," Russian Journal: Vestnik Khirugii, Apr. 1987, (42-45).

Davydov, Y. et al., "Bacteriological and Cytological Assessment of Vacuum Therapy of Purulent Wounds", Vestnik Khirurgii, Oct. 1988, (48-52).

Davydov, Y. et al., "Concepts for Clinical Biological Management of the Wound Process in the Treatment of Purulent Wounds Using Vacuum Therapy," Vestnik Khirugii, Feb. 1991, 132-135).

Davydov, Y. et al., "Vacuum Therapy in the Treatment of Purulent Lactation Mastitis," Russian Journal: Vesnik Khirurgii, Sep. 1986, (66-70).

Davydov, Y. et al., "Vacuum Therapy in treatment of Acute Purulent Diseases of Soft Tissues and Purulent Wounds," Vestnik Khirurgii, (Surgeon's Herald), Medicine Publishers, 1986.

\* cited by examiner

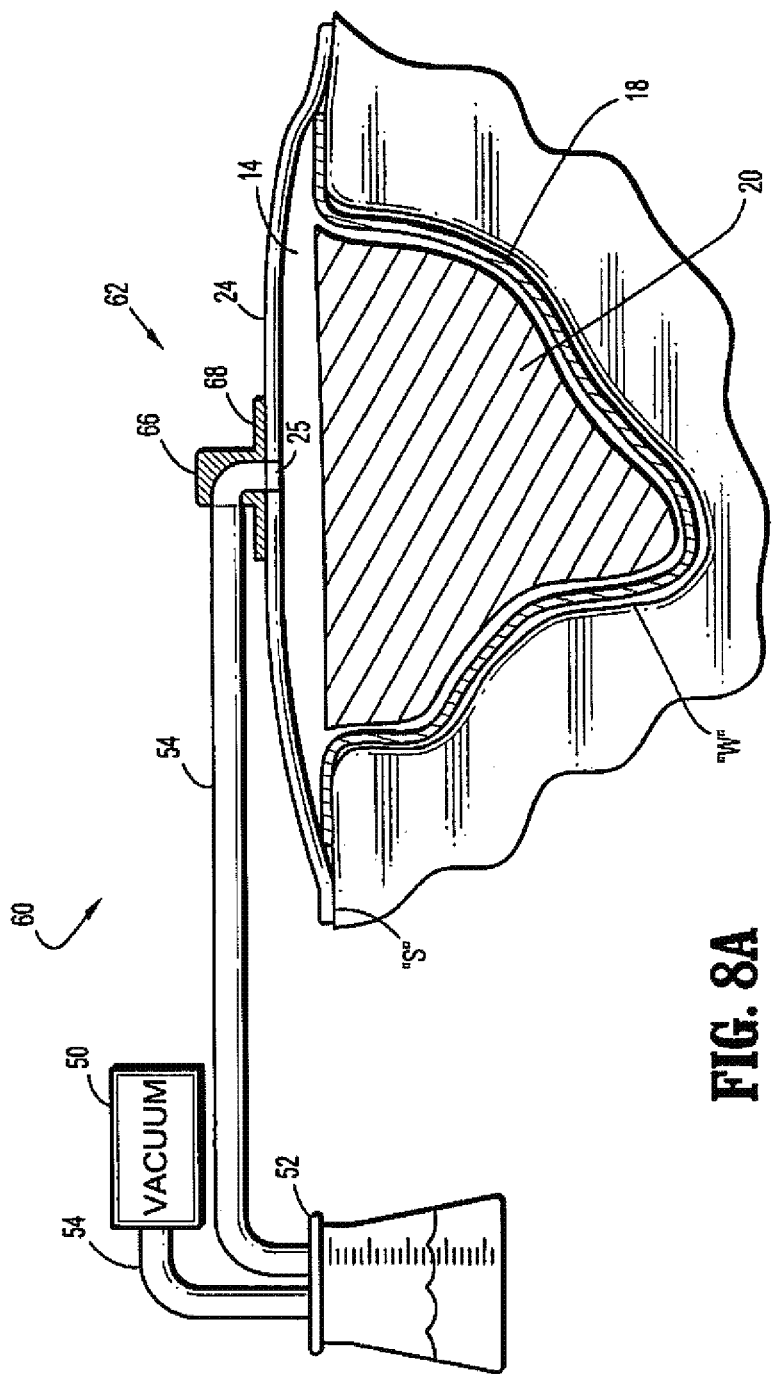
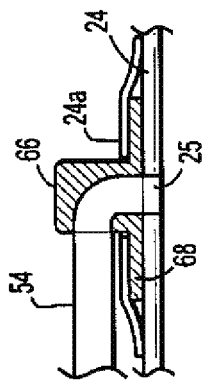
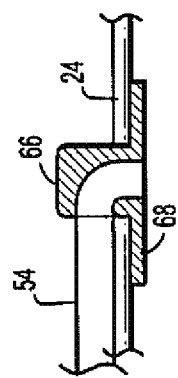
FIG. 8A
FIG. 8B
FIG. 8C

APPARATUS FOR VACUUM BRIDGING AND/OR EXUDATE COLLECTION

CROSS-REFERENCE TO RELATED APPLICATIONS

This application is a divisional application of U.S. application Ser. No. 13/552,000, filed Jul. 18, 2012, which is a continuation application of U.S. application Ser. No. 12/486,858, filed Jun. 18, 2009. The disclosures of these prior applications are hereby incorporated by reference in their entirety.

BACKGROUND

1. Technical Field

The present disclosure relates generally to wound therapy, and, in particular, relates to an apparatus for vacuum bridging and/or exudate collection for managing wound exudates during negative pressure wound therapy.

2. Background of Related Art

Various techniques to promote healing of a wound involve providing suction to the wound. For example, a vacuum source may serve to carry wound exudates away from a wound, which may otherwise harbor bacteria that inhibit the body's natural healing process. One technique for promoting the natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, which stimulates the formation of granulation tissue and the migration of healthy tissue over the wound. This technique has proven effective for chronic or non-healing wounds, but, has also been used for other purposes such as post-operative wound care.

SUMMARY

Accordingly, the present disclosure relates to further developments in wound therapy. In accordance with one embodiment, an apparatus for promoting the healing of an exuding wound includes a cover layer for positioning over a wound to define a reservoir over the wound. An exudate conduit having a fibrous core includes a plurality of fibers communicates with the reservoir for wicking fluids away from the wound. The exudate conduit may include a wound end adapted for positioning proximate to the cover layer and a vacuum end adapted for fluid connection with a vacuum source. A vacuum source may be in fluid communication with the vacuum end of the exudate conduit and operable to establish a reduced pressure within the reservoir. A collection canister may be adapted for fluid connection to the vacuum end of the exudate conduit whereby the vacuum source draws a vacuum through the collection canister.

In one embodiment, at least some of the fibers within the exudate conduit may be at least partially exposed adjacent the wound end of the exudate conduit. The exudate conduit may include an outer sleeve for at least partially accommodating the fibrous core with some of the fibers extending beyond the outer sleeve. At least one of the fibers may comprise a hydrophobic material.

The fibrous core may include an inner bundle of fibers and an outer bundle of fibers. The inner bundle may comprise hydrophobic fibers for discouraging fluid absorption and the outer bundle may comprise hydrophilic fibers for promoting fluid absorption. In the alternative, the outer bundle of fibers is knitted, woven, or braided around the inner bundle of fibers. The fibrous core may include at least one additive. The additive may be one of an antimicrobial, an anti-septic, and a surfactant. The fibrous core may include a concentration of the additive adjacent the wound end which is greater than a concentration of the additive adjacent the vacuum end.

The outer sleeve may comprise a semi-permeable material. In one embodiment, the outer sleeve defines a first cross-sectional dimension greater than a second cross-sectional dimension to thereby reduce the profile of the outer sleeve.

A method for facilitating healing of a wound is also disclosed. The method includes the steps:
applying a wound dressing over a wound;
fluidly connecting an exudate conduit having a fibrous core to the wound dressing;
extending the exudate conduit into a second reservoir that incorporates a vacuum port; and
connecting the second reservoir to a vacuum source via the vacuum port thereby connecting the vacuum source with the first reservoir via the exudate conduit.

According to another aspect of the disclosure, a composite wound dressing apparatus includes a cover layer for defining a reservoir over a wound in which a negative pressure may be maintained by forming a substantially fluid-tight seal around the wound. The cover layer includes an aperture therein through which fluids may be extracted from the reservoir. An elongate wick has a first end and a second end, wherein the first end is in fluid communication with the reservoir through the aperture in the cover layer, and the second end is disposed remotely with respect to the aperture in the cover layer. The elongate wick is adapted for longitudinal transport of fluids therethrough. A flexible wick cover extends over the elongate wick and has a first end and a second end. The first end of the wick cover is configured for forming a substantially fluid tight seal over the aperture in the cover layer, the second end including an aperture therein through which fluids may be extracted from the elongate wick. A fluid port is coupled to the wick cover and is in fluid communication with the second end of the elongate wick through the aperture in the wick cover. The fluid port is configured to receive a fluid conduit at the remote location with respect to the wound.

The apparatus may include a skin covering positioned beneath at least a portion of the elongated wick to substantially minimize contact of fluids with a skin surface adjacent the wound. The skin covering may be adapted to define an enclosure for accommodating the portion of the elongated wick.

The wick cover may include indicia thereon to indicate a distance from the fluid port. The indicia may include rule marks centrally located on the wick cover. The fluid port may include a flange coupled to an underside of the wick cover.

The elongate wick may be constructed of continuous synthetic fibers arranged as an elongate rope. The elongate wick may be treated with an antimicrobial agent such as polyhexamethylene biguanide.

According to another aspect of the disclosure, a composite bridge dressing and delivery apparatus includes a wick cover having a lower surface and an upper surface, wherein the lower surface is at least partially coated with a pressure sensitive adhesive such that the wick cover may form a fluid tight seal with the skin of a patient. An elongate wick is adhered to the lower surface of the wick cover, wherein the elongate wick is adapted for longitudinal transport of fluids therethrough. A backing layer is adhered to the lower surface of the wick cover in a releasable manner such that the elongate wick is interposed between the wick cover and the backing layer.

The wick cover may include an aperture therein through which wound fluids may be drawn. A fluid port may be coupled to the wick cover, wherein the fluid port is configured to provide fluid communication between a vacuum source and the elongate wick through the wick cover. A releasable delivery layer may be adhered to the upper surface of the wick cover. At least one of the wick cover, the backing layer and the delivery layer may include indicia thereon to indicate a length along the apparatus. Identifiers may be included to provide visual queues to indicate the order in which layers of the apparatus should be separated. The apparatus may have a length in excess of 9 inches.

According to another aspect of the disclosure, a negative pressure wound therapy apparatus includes a cover layer for defining a reservoir over a wound in which a negative pressure may be maintained by forming a substantially fluid-tight seal around the wound. The cover layer includes an aperture therein through which fluids may be extracted from the reservoir. An elongate wick has a first end and a second end, wherein the first end is in fluid communication with the reservoir through the aperture in the cover layer, and the second end is disposed remotely with respect to the aperture in the cover layer. The elongate wick is adapted for longitudinal transport of fluids therethrough. A flexible wick cover extends over the elongate wick and has a first end and a second end. The first end of the wick cover is configured for forming a substantially fluid tight seal over the aperture in the cover layer, and the second end of the wick cover includes an aperture therein through which fluids may be extracted from the elongate wick. A vacuum source is in fluid communication with the reservoir, wherein the vacuum source is suitable for generating the negative pressure in the reservoir.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 8A is a cross sectional view of an NPWT treatment apparatus including a fluid port in the vicinity of a vacuum reservoir for treating a wound;

FIG. 8B is a partial cross sectional view of the fluid port of FIG. 8A affixed in an alternate configuration;

FIG. 8C is a partial cross sectional view of the fluid port of FIG. 8A affixed in another alternate configuration;

DETAILED DESCRIPTION OF THE EMBODIMENTS

The NPWT system of the present disclosure incorporates a flexible, low profile exudate conduit having an appropriate fitting for connection to a vacuum source. The sleeve of the exudate conduit includes a collection of fibers disposed therein for wicking fluid away from a wound under vacuum. The sleeve may also hold wound fluid as it is drawn towards the vacuum source thereby acting as a fluid collection vessel.

One NPWT protocol involves covering the wound with a flexible cover layer such as a polymeric film, for example, to establish a vacuum reservoir over the wound where a reduced pressure may be applied by individual or cyclic evacuation procedures. Two methods of delivering the reduced pressure to a wound are either by placing a tube structure through the cover layer into the wound bed such that the tube is surrounded by a suitable fill material, such as gauze or foam, and covering the wound with an adhesive coated thin film to seal the wound area, or by packing and sealing the wound with a suitable fill material, covering the wound with an adhesive coated thin film to seal the wound, and attaching a vacuum connection to the outer film surface of the cover layer. The vacuum connections that are attached to the film dressing may be molded polymer materials that can be rigid or semi-rigid. Often times, however, the location of the wound makes it undesirable to use a tube or rigid vacuum connection because resultant pressure points from the connection may potentially cause further damage to the wound area or impede wound healing. In this situation, a technique known as bridging, in which the same or similar materials are used to fill and seal the wound to form a low-profile channel running away from the wound site to an area where connection to the vacuum source, may be less problematic for the patient and potentially less damaging to the wound. A conventional technique requires a significant amount of the clinician's time custom building the structure. It also requires an increase in treatment costs through the consumption of more and sometimes different dressing materials.

Figure 1:
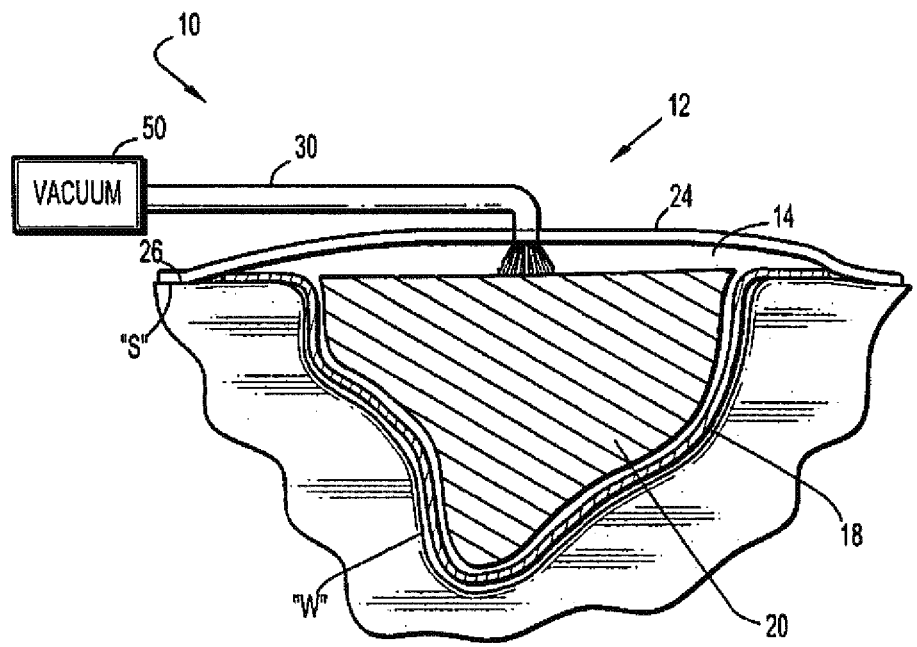
FIG. 1 is a cross sectional view of an NPWT apparatus in accordance with the present disclosure.

Referring initially to FIG. 1, an NPWT apparatus according to the present disclosure is depicted generally as 10 for use on a wound "w" surrounded by healthy skin "s." The NPWT apparatus 10 includes a wound dressing 12 positioned relative to the wound "w" to define a reservoir 14 in which a negative pressure appropriate to stimulate healing may be maintained.

Wound dressing 12 may include a contact layer 18 positioned in direct contact with the bed of wound "w" and may be formed from perforated film material. An appropriate perforated material permits the negative pressure applied to the reservoir to penetrate into the wound "w," and also permits exudates to be drawn through the contact layer 18. A non-adherent material may be selected such that contact layer 18 does not tend to cling to the wound "w" or surrounding tissue when it is removed. Exemplary materials that may be used as a contact layer 18 is sold under the trademark XEROFORM®, CURITY®, and VENTEX® by Tyco Healthcare Group LP (d/b/a Covidien).

Wound filler 20 is positioned in the wound "w," over the optional contact layer 18, and is intended to allow wound dressing 12 to absorb and capture wound exudates. Wound filler 20 is conformable such that it may assume the shape of any wound "w" and may be packed up to the level of healthy skin "s." Exemplary materials that may be used as wound filler 20 are sold under the trademarks KERLIX®, EXCILON®, and WEBRIL®, all by Tyco Healthcare Group LP (d/b/a Covidien).

Wound dressing 12 also includes a cover layer 24 in the form of a flexible membrane. Cover layer 24 may be positioned over the wound "w" such that a biocompatible adhesive at the periphery 26 of the cover layer 24 forms a substantially fluid-tight seal with the surrounding skin "s." Thus, cover layer 24 may act as both a microbial barrier to prevent contaminants from entering the wound "w," and also a fluid barrier maintaining the integrity of vacuum reservoir 14. Cover layer 24 may be formed from a moisture vapor permeable membrane to promote the exchange of oxygen and moisture between the wound "w" and the atmosphere. A membrane that provides a sufficient moisture vapor transmission rate (MVTR) is a transparent membrane sold under the trade name POLYSKIN® II by Tyco Healthcare Group LP (d/b/a Covidien). A transparent membrane permits an assessment of wound conditions to be made without requiring removal of the cover layer 24. Alternatively, cover layer 24 may comprise an impermeable membrane 24. Cover layer 24 may be a substantially rigid member.

Exudate conduit 30 provides a fluid flow path leading through apparatus 10. Exudate conduit 30 may be positioned within or proximate to reservoir 14 through cover layer 24 which is adapted to receive the exudate conduit 30 in a releasable and fluid-tight manner. Exudate conduit 30 extends from the reservoir 14 to provide fluid communication between the reservoir 14 and vacuum source 50. Exudate conduit 30 may be low profile and flexible to allow for easy adaptation by the user to connect the wound dressing 12 to the vacuum source 50. The low profile reduces pressure points on the patient's skin, thereby reducing the risk of pressure irritation of the skin surface or on the wound itself.

Figure 2:
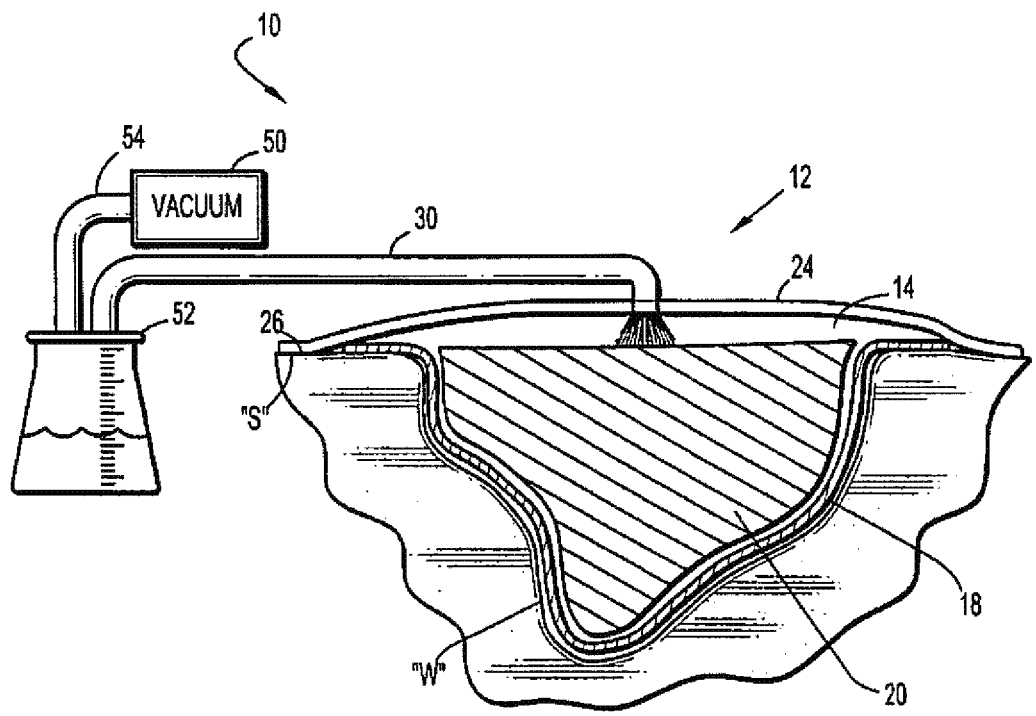
FIG. 2 is a cross sectional view of an NPWT apparatus in accordance with another embodiment of the present disclosure.

In embodiments, a collection canister 52 may extend between reservoir 14 and vacuum source 50 as illustrated in FIG. 2. Fluid conduit 54 extends from collection canister 52 providing fluid communication with vacuum source 50. Any suitable conduit may be used for fluid conduit 54 including those fabricated from elastomeric or polymeric materials. Fluid conduit 54 may connect to vacuum source 50, collection canister 52, or other apparatus components by conventional air tight means such as friction fit, bayonet coupling, or barbed connectors. The conduit connections may be made permanent, or alternatively a quick-disconnect or other releasable means may be used to provide some adjustment flexibility to apparatus 10.

The optional collection canister 52 may comprise any container suitable for containing wound fluids. For example, a rigid bottle may be used as shown or alternatively a flexible polymeric pouch may be appropriate. Collection canister 52 may contain an absorbent material to consolidate or contain the wound drainage or debris. For example, super absorbent polymers (SAP), silica gel, sodium polyacrylate, potassium polyacrylamide or related compounds may be provided within canister 52. At least a portion of canister 52 may be transparent to assist in evaluating the color, quality or quantity of wound exudates. A transparent canister may thus assist in determining the remaining capacity of the canister or when the canister should be replaced.

Vacuum source 50 generates or otherwise provides a negative pressure to the NPWT apparatus 10. Vacuum source 50 may comprise a peristaltic pump, a diaphragmatic pump or other mechanism that is biocompatible and draws fluids, e.g. atmospheric gases and wound exudates, from the reservoir 14 appropriate to stimulate healing of the wound "w." The vacuum source 50 may be adapted to produce a sub-atmospheric pressure in the reservoir 14 ranging between about 20 mmHg and about 500 mmHg, in embodiments, from about 75 mmHg to about 125 mmHg, in other embodiments from about 50 mmHg to about 80 mmHg. Vacuum source 50 may be a peristaltic pump, a diaphragmatic pump or other mechanism that draws fluids, e.g. atmospheric gasses and wound exudates, from the reservoir 14 appropriate to stimulate healing of the wound "w." One suitable peristaltic pump is the Kangaroo PET Enteral Feeding Pump manufactured by Tyco Healthcare Group LP (d/b/a Covidien).

Figure 3:
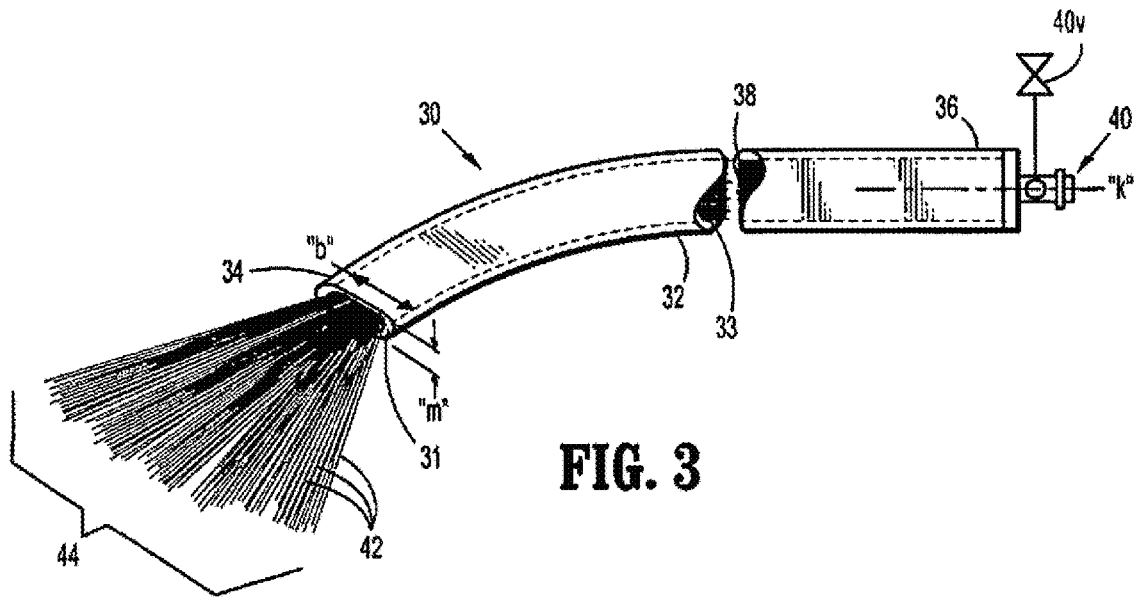
FIG. 3 is perspective view of an exudate conduit containing a fibrous core which forms the connection between the wound and vacuum source of FIG. 1.

Referring now to FIG. 3, exudate conduit 30 includes outer member of sleeve 32 defining lumen 33. Exudate conduit 30 has first or proximal end 34, second or distal end 36, and fibrous core 38 disposed within lumen 33 of outer sleeve 32. Outer sleeve 32 may be fabricated from flexible polymer and/or elastomeric materials, for example, polyolefins such as polypropylene and polyethylene, polyesters such as polyethylene terephthalate, polyamides such as nylon, and polyurethanes. Outer sleeve 32 may be constructed from materials which are non-irritating and biocompatible. In embodiments, outer sleeve 32 may be fabricated from a breathable material, such as a material with a high moisture vapor transmission rate to allow for vapor transmission and evaporation thus increasing the fluid retention capacity of the exudate conduit 30.

The wall 31 of outer sleeve 32 may range in thickness from about 0.002" to about 0.020". The diameter of outer sleeve 32 may be from about 0.1" to about 3" depending on the application. Additionally, outer sleeve 32 may be clear or translucent in color to permit visualization of wound fluid. Exudate conduit 30 may also be opaque and define a transparent window for visualizing the wound fluid. In embodiments, the window may be from about 15% to about 25% of the periphery of outer sleeve 32. Outer sleeve 32 may define a reduced profile with respect to the longitudinal axis "k" of the sleeve 32. For example, outer sleeve 32 defines a first transverse dimension "b" which is substantially greater than a second transverse dimension "m" relative to the longitudinal axis "k." These dimensions provide a generally flattened, planar or elliptical profile to exudate conduit 32. The reduced profile may assist in a bridging technique as will be discussed.

Exudate conduit 30 includes connection member or fitting 40 at the second or distal end 36 that connects to vacuum source 50. Connection member or fitting 40 may be any conventional fitting for forming a fluid and air tight connection between exudate conduit 30 and vacuum source 50. In embodiments, connection member 40 may include a check valve (schematically as reference numeral 40v) and/or filter to prevent fluid contamination of vacuum source 50. Check valves include duck bill style valves that are held in the open position during connection to vacuum source 50 and assume a closed position in the absence of the vacuum pressure thereby preventing wound fluid leakage. Connection member 40 may include electronic moisture sensing capability to signal that the fluid capacity of the conduit is full, thereby triggering an alarm and/or turning the vacuum source off until the conduit is replaced.

Exudate conduit 30 contains fibers 42 therein. A plurality of fibers 44 is disposed within exudate conduit 30 for maintaining the shape and/or preventing the flexible conduit 30 from collapsing. Fibers 42 also facilitates wound fluid movement. Fibers 42 may be any size from a micro denier of about 0.002 to a larger denier of about 0.1. In embodiments, fibers 42 may extend from first or proximal end 34 of exudate conduit 30 into reservoir 14 or wound bed "w."

Figure 4A:
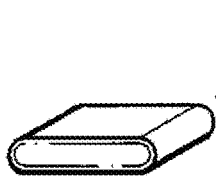
FIGS. 4A-4F are schematic views depicting various cross sections of individual fibers of the exudate conduit of the present disclosure.
Figure 4B:
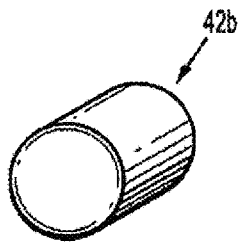
Figure 4C:
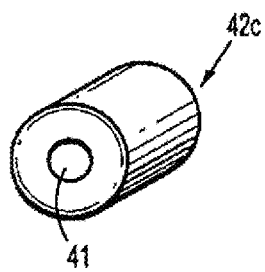
Figure 4D:
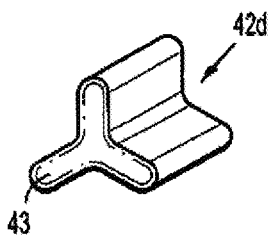

Referring now to FIGS. 4A-4F, the fibers may exhibit various cross-sections to enhance wicking capabilities or other fluid handling characteristics of the exudate conduit 30. In embodiments, the fibers may be constructed to promote fluid movement without the aid of vacuum or gravity. A solid flat 42a or round 42b cross section as depicted in FIGS. 4A and 4B, respectively, may be a standard for most fibers due to a relatively low cost when compared to modified cross sections. Fiber 42c is depicted in FIG. 4C having a void 41 in its cross section. Void 41 runs the entire length of fiber 42c yielding a reduced density and rigidity of fiber 42c and permitting air to be trapped within. Such a cross section may facilitate crimping, entangling and/or lofting processes which may further enhance fluid handling properties of the fiber. A multi-lobal cross section may also be used as depicted in FIG. 4D. Tri-lobal fiber 42d exhibits three arms 43 projecting from a central region offering rigidity and resilience to the fiber 42d.

Figure 4E:
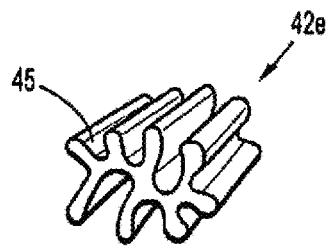
Figure 4F:
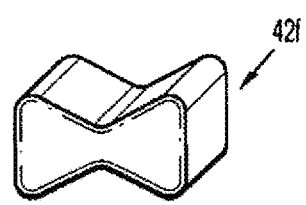

Highly modified cross section fibers 42e as depicted in FIG. 4E are sold under the trade name 4DG™ by Fiber Innovation Technology, Inc. Deep channels 45 of various sizes and configurations are provided along a longitudinal axis of the fiber 42e to help promote capillary wicking with its relatively large surface area. For example, fibers 42e having a 4DG™ cross section have demonstrated a capability to transport up to 2 liters of water per hour per gram of fiber. A fiber 42f having a bowtie cross section as depicted in FIG. 4F may be well suited for use in self-crimping fibers.

Figure 5A:
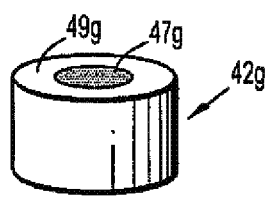
FIGS. 5A-5G are schematic views depicting various co-extrusion arrangements for individual fibers of the exudate conduit of the present disclosure.
Figure 5B:
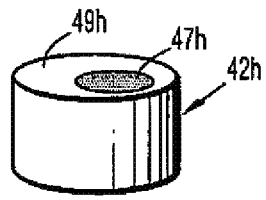
Figure 5C:
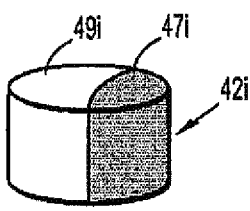
Figure 5D:
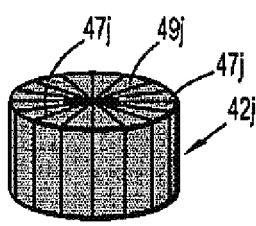
Figure 5E:
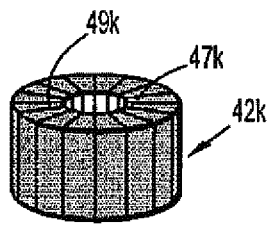

Referring now to FIGS. 5A through 5G, two or more distinct polymers may be co-extruded to generate fibers with complex profiles and specialized characteristics. The co-extruded fibers may have any of the cross-sections as described above, among others. A fiber 42g exhibiting a concentric sheath-core arrangement is depicted in FIG. 5A. A core polymer 47g is surrounded by a sheath polymer 49g. A sheath polymer may exhibit a lower melting temperature than a core polymer such that the sheath polymer may be melted to provide a binder for individual fibers. Other applications for a sheath-core arrangement may include providing a high strength structural core polymer 47g and a sheath polymer 49g with surface characteristics appropriate to help promote wicking of wound fluid or to accept any of the beneficial polymer additives discussed below. A fiber 42h exhibiting an eccentric sheath-core arrangement is depicted in FIG. 5B including an off-center core polymer 47h and corresponding sheath polymer 49h. This arrangement may be used to provide a self-crimping fiber when the core polymer and sheath polymer are provided with differing shrinkage characteristics when subject to a temperature change. When heated, the fibers may curl into a helix that is retained when the filament is cooled, thus developing a crimp or bulk in an otherwise flat fiber. Such a self-crimping procedure may be further facilitated by using a side-by-side arrangement as depicted in FIG. 5C. Fiber 42i is similar to fiber 42h, but differs in that core polymer 47i and sheath polymer 49i each occupy a portion of the outer surface of the fiber 42i. With a proper polymer selection, the side-by-side arrangement of fiber 42i may yield higher levels of latent crimp than the eccentric sheath-core arrangement of fiber 42h. As shown in FIG. 5D, a fiber 42j having a pie-wedge arrangement may include alternating wedges comprising polymers 47j and 49j. A fiber 42k exhibiting a hollow pie wedge arrangement including a hollow center core is depicted in FIG. 5E.

Figure 5F:
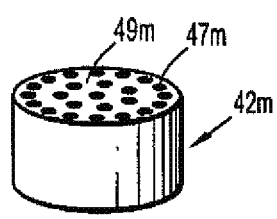
Figure 5G:
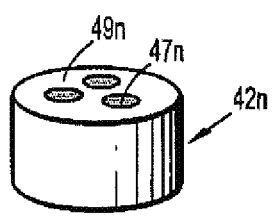

With reference to FIG. 5F, fiber 42m exhibits an islands-in-the-sea arrangement where one or more "island" polymers 47m are surrounded by a soluble "sea" polymer 49m. This arrangement may provide for very fine strands of island polymers 47m to be effectively handled by manufacturing equipment. Once the island polymers 47m are in place, the soluble sea polymer is dissolved away. For example, as many as about 37 or more island polymers 47m having a denier of about 0.04 (roughly 2 microns in diameter) may thus be handled effectively as a single fiber 42m. A fiber 42n exhibits a "three island" arrangement, as depicted in FIG. 5G. This arrangement includes three island polymers 47n surrounded by a sea polymer 49n. Fiber 42n may be used in a manner similar to fiber 42m exhibiting an islands-in-the-sea arrangement, but may be more commonly used in a manner similar to fibers 42g, 42h, and 42i described above exhibiting a sheath-core arrangement. Fiber 42n may be described as including three core polymers 47n collectively having an increased surface area to discourage de-lamination from a potentially incompatible sheath polymer 49n.

Various suppliers may produce fibers as described above, as any commercial fiber or suture material may advantageously be employed in exudate conduit 30. A non-exhaustive list of materials includes, but are not limited to, polymers and polymer blends selected from the group consisting of polyolefins (such as polyethylene and polypropylene including atactic, isotactic, syndiotactic, and blends thereof as well as, polyisobutylene and ethylene-alphaolefins copolymers, and fluorinated polyolefin such as polytetrafluoroethylene); polyesters (such as polyethylene terephthalate and polybutylene terephthalate); acrylic polymers and copolymers; modacrylics; vinyl halide polymers and copolymers (such as polyvinyl chloride); polyvinyl ethers (such as polyvinyl methyl ether); polyvinylidene halides (such as polyvinylidene fluoride and polyvinylidene chloride); polyacrylonitrile; polyvinyl ketones; polyvinyl aromatics (such as polystyrene); polyvinyl esters (such as polyvinyl acetate); copolymers of vinyl monomers with each other and olefins (such as eteylene-methyl methacrylate copolymers, acrylonitrile-styrene copolymers, ABS resins and ethylene-vinyl acetate copolymers); polyamides (such as nylon 4, nylon 6, nylon 6.6, nylon 610, nylon 11, nylon 12 and polycaprolactam); alkyd resins; polycarbonates; polyoxymethylenes; polyimides; polyethers; epoxy resins; aramids, polyurethanes; rayon; rayon-triacetate; and spandex.

Fibers 30 may be bundled into a plurality of fibers 44 to form fibrous core 38. An outer bundle of fibers 46 may be selectively arranged around an inner core or bundle 48 of various fiber combinations and sizes to optimize fluid handling and to reduce the propensity for clogging of wound fluid. It is envisioned that the fibers that comprise the bundles may be varied to facilitate optimal fluid handling. For example, the inner bundle fibers 48 may be a hydrophobic polymer to discourage fluid absorption while the outer bundle fibers 46 may be hydrophilic to promote some absorption.

Figure 6A:
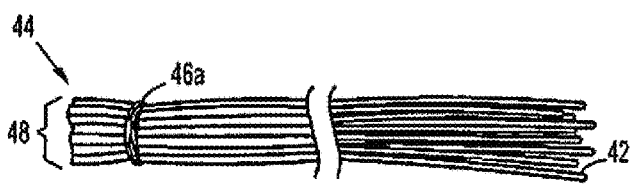
FIGS. 6A-6J are partial orthogonal views depicting various configurations of the fibrous core of the exudate conduit of the present disclosure.
Figure 6B:
Figure 6C:
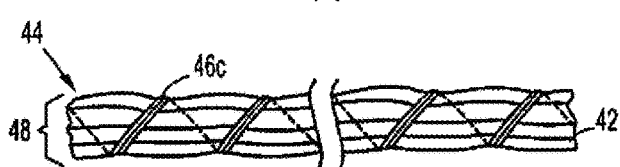

Typical fiber bundle 44 arrangements are illustrated in FIGS. 6A-6E. Referring now to FIG. 6A, fibers 42 may be arranged so as to be generally non-intersecting along their length. Although not necessarily parallel, fibers 42 may be generally free from entanglement or interlacing over a substantial portion of their length. Outer bundle of fibers 46a may be included to help prevent separation of fibers 42 which form inner bundle 48. A single outer bundle 46a may be formed from a separate continuous fiber wrapped or tied around inner bundle 48 to compress bundle 48 in a localized region. Alternatively, outer bundle 46b may be placed intermittently along inner bundle 48, as shown in FIG. 6B, to help secure fibers 42 at multiple locations, or separate continuous fibers may be wrapped helically around inner bundle 48 as in FIG. 6C to form outer bundle 46c.

Figure 6D:
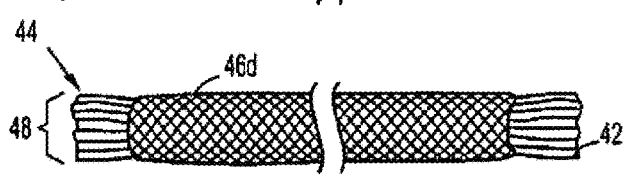
Figure 6E:

Fibers 42 may also be enclosed in a knitted, woven, or braided outer bundle 46d as illustrated in FIG. 6D. The knitted, woven, or braided outer bundle 46d may be adjusted to provide a greater or lesser diameter and conduit patency under vacuum or kinking of the exudate conduit. Fibers may also be twisted, as in a rope, to provide an outer bundle 46e as illustrated in FIG. 6E.

Figure 6F:
Figure 6G:
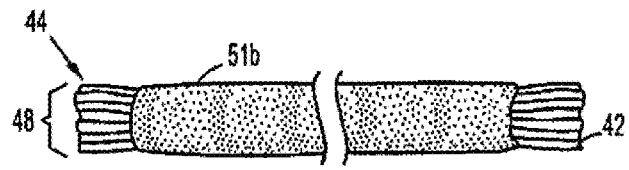

Alternatively, fibers 42 may be arranged or constructed as shown in FIGS. 6F-6J to help the inner bundle 48 resist separation of individual fibers 42. Fibers 42 may be enclosed with a self-sealing, non-woven mesh or other porous sheet to form bonding feature 51a as shown in FIG. 6F. A self-sealing bonding feature 51a may be an elastic or slightly undersized band such that individual fibers 42 may be inserted through an open end of the band to be constrained under compression. Alternatively, bonding features may include an adhesive component such that a flat strip may be wrapped around the fibers and the flat strip may be affixed by adhering either to itself or to the individual fibers 42 with the adhesive component. As depicted in FIG. 6G, a bonding feature 51b may be formed with a substantial length of a non-woven mesh or a porous sheet to enclose a substantial length of the fibers. Bonding features 51a and 51b may be porous to promote absorption of wound fluids and exudates.

Figure 6H:
Figure 6I:
Figure 6J:

Fibers 42 which form inner bundle 48 may be entangled by various processes to form a bonding feature 51c (FIG. 6H). Jets of steam, air, or water may be directed at localized regions in the bundle 48 to entangle fibers 42 and provide bonding feature 51c. The entangling process may involve application of heat in a localized area to entangle or bond fibers 42. Another example of an entangling process involves needles used in a manner similar to needle punching to entangle fibers 42. A bonding feature 51d (FIG. 6I) may be provided simply by bonding fibers 42 with an adhesive, or by incorporating a binding material having a lower melting temperature than fibers 42. By heating the bundle, the binding material may melt and bind fibers 42 together upon cooling. A binding material may be provided along with one or more of the individual fibers in a co-extrusion such as a core-sheath arrangement, as described above. As depicted in FIG. 6J, a bonding feature 51e may also be provided by crimping individual fibers to provide some degree of entanglement thereby providing additional surface area, as described in greater detail above. It is also envisioned that the arrangement of individual fibers may include two or more of the features shown in FIGS. 6A through 6J.

Various polymer additives may be applied to individual fibers 42, the inner bundle 48, the outer bundle 46, or the entire plurality of fibers 44 or a selective subset of fibers therein. Further, the additive may be imparted to a section of each fiber such as the sheath construction of a sheath-core fiber construct. The additive may be any substance or mixture of substances that have clinical use. Consequently, the additives may or may not have pharmacological activity per se, e.g., a dye. Alternatively an additive could be any agent that provides a therapeutic or prophylactic effect, a compound that affects or participates in tissue growth, cell growth, cell differentiation, a compound that may be able to invoke a biological action such as an immune response, or could play any other role in one or more biological processes. It is envisioned that the additive may be applied to the fibers 42 in any suitable form of matter, e.g., films, powders, liquids, gels and the like. The additive could also be formed to activate only on contact with moisture such as wound fluids and exudates.

Examples of classes of additives which may be utilized in accordance with the present disclosure include anti-adhesives, antimicrobials, antibacterials, antibiotics, anti-virals, anti-fungals, anti-septics, anti-inflammatories, and anesthetics. Additionally, odor control technology may also be incorporated into fibers 42 as an additive. It is also intended that combinations of additives may be used. For example, an anti-adhesive, to prevent adhesions from forming between the fibers and the surrounding tissue, may be utilized with an antimicrobial, such as polyhexamethylene biguanide, to reduce the bio burden in the wound bed.

Other additives, such as surfactants like silicone or floropolymers such as PTFE may be added to provide fiber 42 with a slicker surface. A slicker or surfactant treated surface may facilitate optimal fluid handling properties. For example, a surfactant or combination of surfactants may create a highly hydrophobic surface on the fiber and/or bundle to encourage directional wicking and fluid movement away from the wound dressing. Surfactant treatment may be selective along the length of fiber 42 such that the portions located within or adjacent the proximal end 34 of exudate conduit 30 could be processed in a combination of materials or concentration of materials to promote more rapid fluid movement away from the wound where the portions of fibers 42 located in or towards the distal end 36 of exudate conduit 30 would allow slower movement thus increasing its capacity of holding and containing wound fluid.

In embodiments, exudate conduit 30 may be treated with a moisture sensitive material on the inside of sleeve 32 and/or fiber bundle 44 that could change color in the presence of moisture, thus indicating a filled conduit. The color sensitive material could be continuous providing a visual indication of the remaining fluid capacity of the conduit. The distal end 36 of sleeve 32 may be treated to provide an early indication of the conduit's capacity. As such, exudate conduit 30 may act as a fluid reservoir thus eliminating the need for collection canister 52 at or near vacuum source 50. The exudate conduit 30 may vary in length to accommodate larger quantities of wound fluid.

Figure 7:
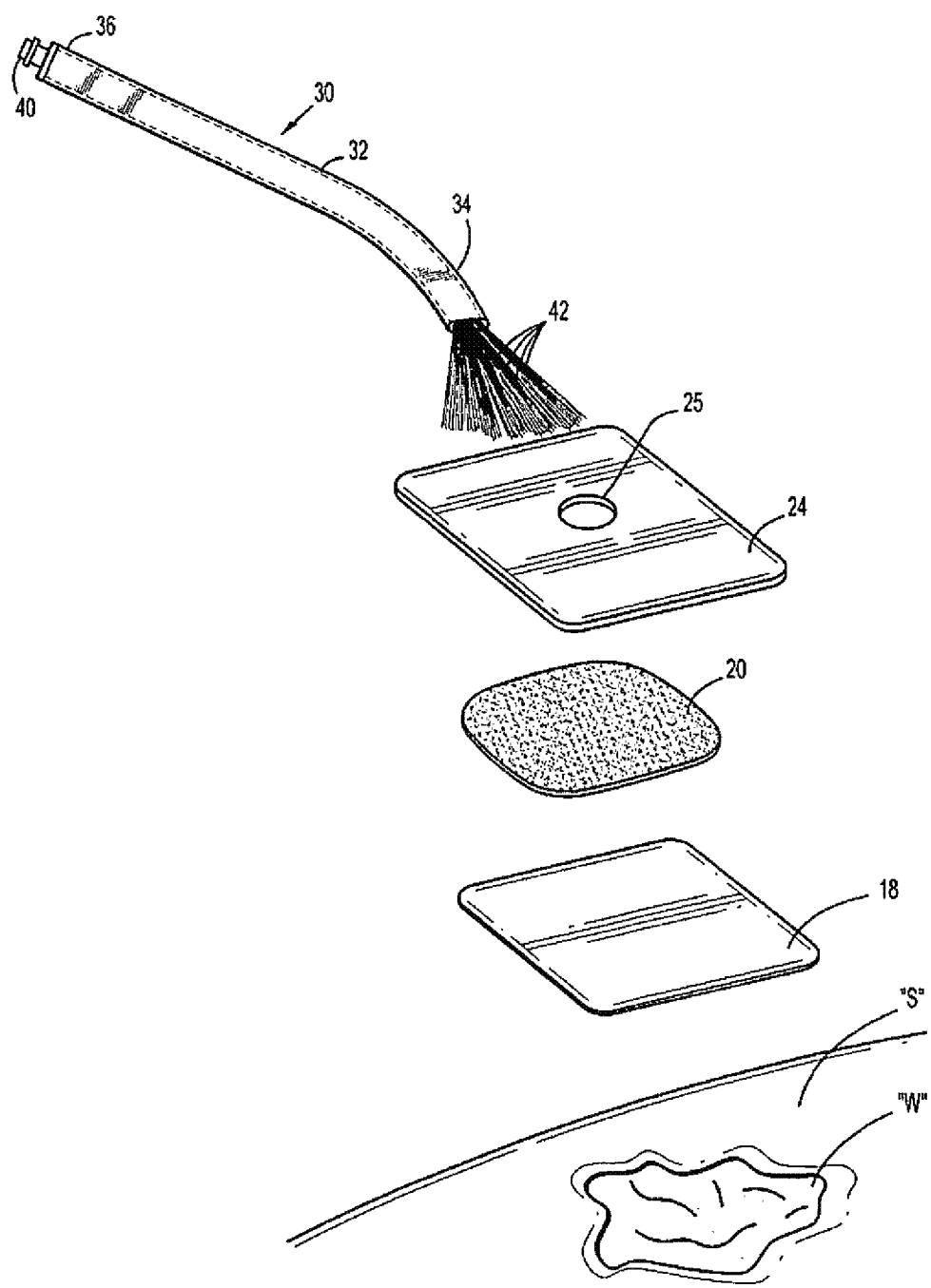
FIG. 7 is a perspective view, with parts separated, of the exudate conduit and wound dressing in accordance with the present disclosure.

Referring now to FIG. 7, the fibers 42 of exudate conduit 30 are at least partially inserted through an aperture or access hole 25 in cover layer 24 thereby positioning the fibers proximate to the wound "w." Access hole 25 may be provided as a prefabricated feature of cover layer 24, or alternatively, access hole 25 may be cut as appropriate by a clinician at the time cover layer 24 is installed. Proximal end 34 of sleeve 32 may then be inserted into or adjacent to access hole 25. Sleeve 32 may be provided with an adhesive for securing the exudate conduit 30 to cover layer 24 in order to form an air and fluid tight connection with cover layer 24. Alternatively, an adhesive coated thin film, thin film dressing, or other provisions may be made for sealing the connection between exudate conduit 30 and access hole 25 of cover layer 24. Distal end of sleeve 32 may then be routed to the vacuum source or collection canister as discussed above.

The size, shape, and/or location of the wound "w" may influence the manner in which exudate conduit 30 is routed relative to wound dressing 12 and the vacuum source 50. For example, some wounds "w" may accommodate a fluid port or a vacuum port in the vicinity of a vacuum reservoir as depicted in FIG. 8A.

FIG. 8A generally depicts an NPWT apparatus 60 for use on a wound "w" surrounded by healthy skin "s." The NPWT apparatus 60 includes a wound dressing 62 positioned relative to the wound "w" to define a reservoir 14 in which a negative pressure appropriate to stimulate healing may be maintained.

Wound dressing 62 includes a contact layer 18 positioned in direct contact with the bed of wound "w." Contact layer 18 may be formed from perforated film material as described above with reference to FIG. 1. Also, passage of wound fluid through the contact layer 18 is preferably unidirectional such that exudates do not flow back into the wound bed. Unidirectional flow may be encouraged by conical or directional apertures formed in the contact layer 18, or a lamination of materials having absorption properties differing from those of contact layer 18. Wound dressing 62 also includes a wound filler 20 and a cover layer 24 as described above with reference to FIG. 1. Cover layer 24 includes access hole 25 therein, through which wound fluids and atmospheric gasses may be removed from the dressing 62.

A fluid port 66 having a flange 68 may also be included in wound dressing 62 to facilitate connection of the wound dressing 62 to fluid conduit 54. The fluid port 66 may be configured as a rigid or flexible, low-profile component, and may be adapted to receive a fluid conduit 54 in a releasable and fluid-tight manner. An adhesive on the underside of flange 68 may provide a mechanism for affixing the fluid port 66 to the dressing 62, or alternatively the flange 68 may be positioned within reservoir 14 (FIG. 8B) such that an adhesive on an upper side of the flange 68 affixes the fluid port 66. As depicted in FIG. 8C, an additional alternative for affixing the fluid port to the cover layer 24 involves securing the flange 68 to the cover layer 24 with a skirt 24a. The skirt 24a may be constructed of an adhesively coated polymeric film similar to the cover layer 24. However it is affixed to the dressing 62, a hollow interior of the fluid port 66 provides fluid communication between the fluid conduit 54 and the reservoir 14.

Fluid conduit 54 extends from the fluid port 66 to provide fluid communication between the reservoir 14 and collection canister 52. Any suitable conduit may be used including exudate conduit 30 described above with reference to FIG. 3. Leading from collection canister 54 is another section of fluid conduit 54 providing fluid communication with vacuum source 50.

In some applications, providing a fluid port or exudate conduit at a remote location with respect to the wound "w" may be beneficial. For example, wounds formed on contoured body parts, such as the foot or elbow, or other parts of the body in which the fluid port or exudate conduit would inhibit the patient's movement or comfort may require a different and sometimes indirect method of routing exudate conduit 30. The exudate conduit 30, then, may be routed from the wound site to a second site where connection to the vacuum source is less problematic for the patient and less damaging to the wound.

Figure 9:
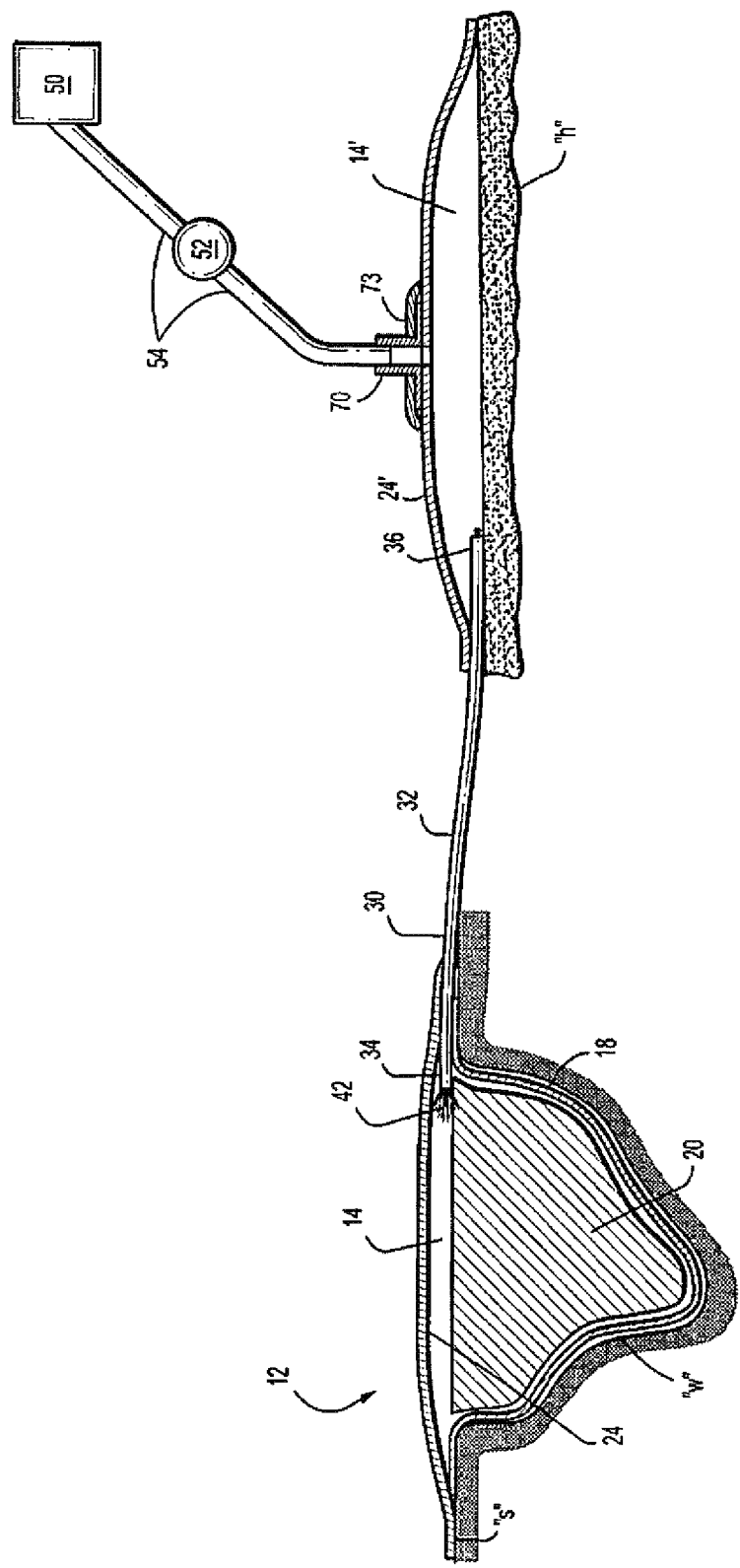
FIG. 9 is a sectional view of an NPWT apparatus in accordance with another embodiment of the present disclosure.

As illustrated in FIG. 9, a wound dressing 12 is positioned relative to a wound "w" to define a reservoir 14 in which a negative pressure appropriate to stimulate healing may be maintained as described above with reference to FIGS. 1 and 2. Exudate conduit 30 may be positioned through cover layer 24 in any manner and position which will not interfere with the patient or wound healing. As illustrated, the proximal end 34 of sleeve 32 is positioned within reservoir 14 by sealing the conduit 30 between skin "s" and cover layer 24 in a fluid and air tight manner. Exudate conduit 30 may then be routed to run along the healthy skin "s" of the patient to prevent or minimize any unnecessary winding or flexure that could tend to kink the exudate conduit 30. In embodiments, an exudate conduit 30 having an outer sleeve 32 with a reduced profile as discussed above may be positioned with the "flattened" side having the first transverse dimension "b" substantially flush with skin "s" to maximize the exudate conduit's contour along skin "s" of the body. Thus, exudate conduit 30 may be placed along the patient's skin "s", such as up a leg, down an arm, or across a chest, towards a second site which does not interfere with the patient's movement or comfort, such as an such as a portion of healthy skin "h" that is relatively flat, for connection to vacuum source 50.

The second site may be any area where a vacuum port 70 may be placed for connection to a vacuum source 50. As illustrated, a second cover layer 24' may be placed over skin "h" to form a second reservoir 14'. The distal end 36 of the exudate conduit 30 may be sealed within the reservoir 14' by cover layer 24' in a similar or different manner than that of proximal end 34 with cover layer 24. A vacuum port 70 having a flange 73 may be provided to facilitate connection of the reservoir 14' to vacuum source 50 via fluid conduit 54. The vacuum port 70 is affixed to cover layer 24' and a hollow interior of the vacuum port 70 provides fluid communication between the fluid conduit 54 and the reservoir 14'. The fluid conduit 54 may then be routed to a canister or vacuum source as described in detail above.

Figure 10A:
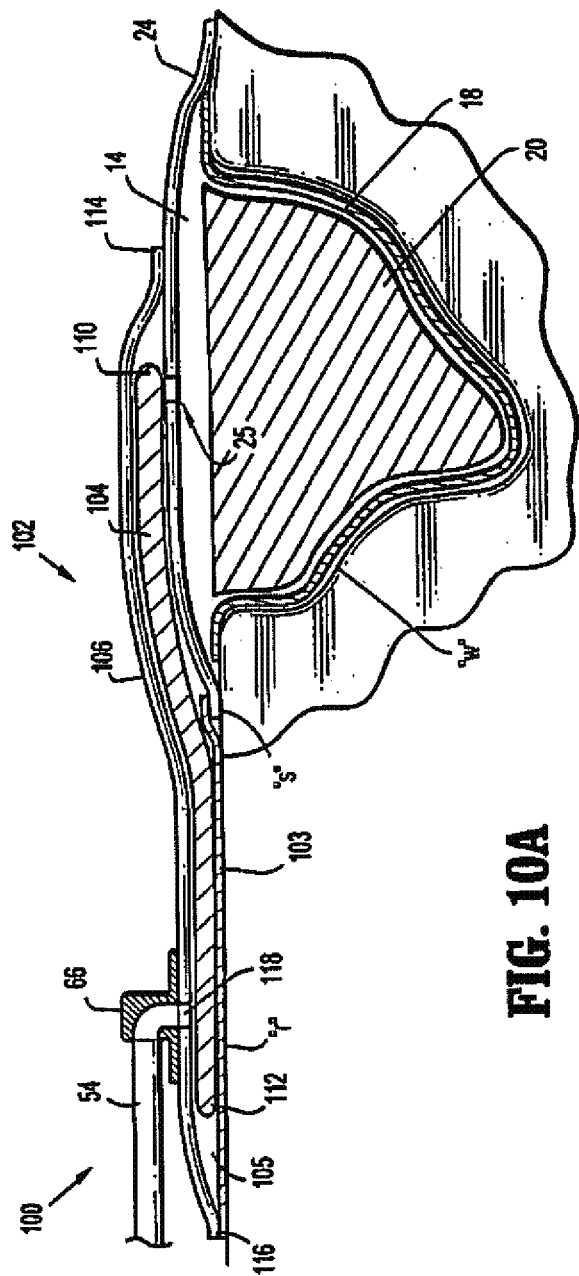
FIG. 10A is a cross sectional view of a composite wound dressing and bridging dressing with the fluid port in a remote location in accordance with the present disclosure as applied on the wound.

Referring now to FIG. 10A, an alternate embodiment includes a composite wound dressing 100. Compound dressing 100 permits a fluid port 66 to be placed remotely with respect to the wound "w." Composite wound dressing 100 includes a contact layer 18, a wound filler 20 and a cover layer 24 applied to the wound "w" in a manner similar to wound dressing 12 discussed. The fluid port 66, however, is affixed to the composite wound dressing 100 at a location "r" that is remote from the wound "w," rather than being affixed to the cover layer 24 at the access hole 25.

To provide fluid communication, or a "bridge," between access hole 25 and the remote location "r," a bridging dressing 102 is positioned partially over the cover layer 24 and partially over the healthy skin "s." The remote location "r" may be an area of the healthy skin "s" where the fluid port 66 will tend not to irritate the wound "w" or to cause discomfort for the patient. If the wound "w" is located on the back of a patient, the remote location "r" may be, for example, at the chest or shoulder of the patient. This permits the patient to lie comfortably without placing undue pressure on the fluid port 66. To provide this functionality, a bridging dressing 102 may exhibit a length in the range from about 2 inches to about 12 inches, or more.

The bridging dressing 102 includes a, skin lining or film 103, an elongate wick 104, a wick cover 106, and the fluid port 66. The film or lining 103 will be placed in contact with skin, typically, the healthy skin along a portion of the "bridge". The lining or film 103 may be any suitable film adapted for patient contact, and may or may not have an adhesive backing for securement to the skin. The film or lining 103 may overlap a peripheral portion of the cover 24. The film or lining 103 may or may not be adhesively coated, and, in some embodiments is a thin, transparent, polymeric membrane such as polyurethane, elastomeric polyester or polyethylene. The elongate wick 104 defines a longitudinal direction therealong between a first end 110 positioned near the access hole 25 in the cover layer 24, and a second end 112 near the remote location "r." The elongate wick 104 is adapted for longitudinal transport of fluids therethrough. The elongate wick 104 may promote capillary action in a longitudinal direction to provide for the longitudinal transport of fluids. A cross section of individual fibers, or an arrangement of fibers may serve to transport fluids longitudinally. The elongate wick 104 may be constructed from materials suitable for use as wound filler 20 and/or exudate conduit 30. The elongate wick 104 may, for example, be constructed of hydrophobic fibers, such as continuous synthetic fibers, arranged as an elongate rope or cord. The fibers may be crimped, bulked or lofted to influence the absorptive, wicking or comfort characteristics of the elongate wick 104. U.S. Provisional Application No. 61/188,370, filed Aug. 8, 2008, the entire content of which is hereby incorporated by reference, describes various such processes and arrangements for fibers, which may be employed to construct the elongate wick 104 or the filler 20.

Alternatively, elongate wick 104 may be constructed from staple fibers, and may be arranged as woven or kitted fabrics. The fibers may be treated with antibacterial agents such as polyhexamethylene biguanide (PHMB) to decrease the incidence of infection, or other medicaments to promote healing of the wound "w." The fibers may also include combinations of materials or chemicals to tailor the wick for specific fluid transport, comfort or other specific requirements.

The wick cover 106 has a first end 114 positioned near the access hole 25 in the cover layer 24 and beyond the first end 110 of the elongate wick 104. A second end 116 of the wick cover 106 is positioned near the remote location "r." The first end 114 of wick cover 106 forms a substantially fluid-tight seal with the cover layer 24, and the second end 116 of the wick cover 106 forms a substantially fluid tight seal with the lining 103 or the skin in the absence of the lining 103. The second end 114 of wick cover 106 may contact or be secured to lining 103 thereby assisting in securement of the lining relative to the subject and optionally forming an enclosure 105 between the wick cover 106 and the lining 103 substantially enclosing the a portion of the elongated wick 103 preventing exudate from contacting the skin.

Wick cover 106 may be constructed from any of the materials used to fabricate cover layer 24. For example, wick cover 106 may be constructed of an adhesively coated, thin, transparent, polymeric membrane such as polyurethane, elastomeric polyester or polyethylene. The thickness of the wick cover 106 may, for example, be in the range of about 0.8 mils to about 1.2 mils. Thicknesses in this range may permit wick cover 106 to conform comfortably to the contours of a patient's skin surrounding the elongate wick 104, and accommodate evacuation cycles associated with an NPWT procedure. The adhesive coating should provide firm, continuous adhesion to the skin "s" and/or the cover layer 24 such that leak paths are not readily formed as reservoir 14 is subjected to the evacuation cycles of an NPWT treatment. The adhesive should also not unduly interfere with the MVTR of the wick cover, and should peel away from the skin "s" easily when the wick cover 106 is no longer required.

An aperture 118 in the wick cover 106 facilitates fluid communication between fluid port 66 and the elongate wick 104. The fluid port 66 forms a substantially fluid tight seal with the wick cover 106 near the aperture 118 and receives fluid conduit 54. Fluid conduit 54 may be coupled to a vacuum source 50 as described above with reference to FIG. 2.

In this manner, fluids such as wound exudates and atmospheric gasses may be drawn from the reservoir 14, through the access hole 25 in the cover layer 24, and into the first end 110 of the elongate wick 104. The fluids are transported longitudinally through the wick 104 under the influence of the reduced pressure and the fluid transport properties of the wick 104 to the second end 112 of the wick 104 near the remote location "r." The fluids may then be removed from the bridging dressing 102 through the fluid port 66. Since the wick 104 and the wick cover 106 are generally more flexible and conformable to the contours of the patient's body, and also to the movements of the patient than fluid port 66, these components of bridging dressing 102 are typically more comfortable positioned adjacent to the wound "w."

Figure 10B:
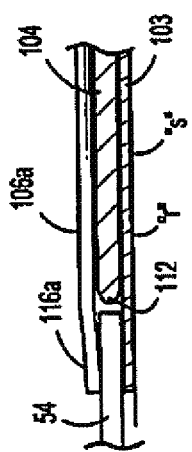
FIG. 10B is a partial cross-sectional view of an alternate configuration of a bridging dressing applied without a fluid port.

Referring now to FIG. 10B, an alternate embodiment of the disclosure permits fluid communication between the fluid conduit 54 and the second end 112 of the wick 104 near the remote location "r" to be established without the use of a fluid port. A wick cover 106a includes a second end 116a devoid of an aperture for the attachment of a fluid port. Rather, the wick cover 106a forms a substantially fluid tight seal with the fluid conduit 54 and the lining 103 surrounding the remote location "r." This configuration allows fluid conduit 54 to be placed comfortably at the remote location "r" rather than near the wound "w." Since the fluid conduit 54 may be generally less conformable or more rigid than the wick 104 and the wick cover 106a, placement of the fluid conduit 54 remote from the wound "w" may be more comfortable than adjacent the wound "w."

Figure 11:
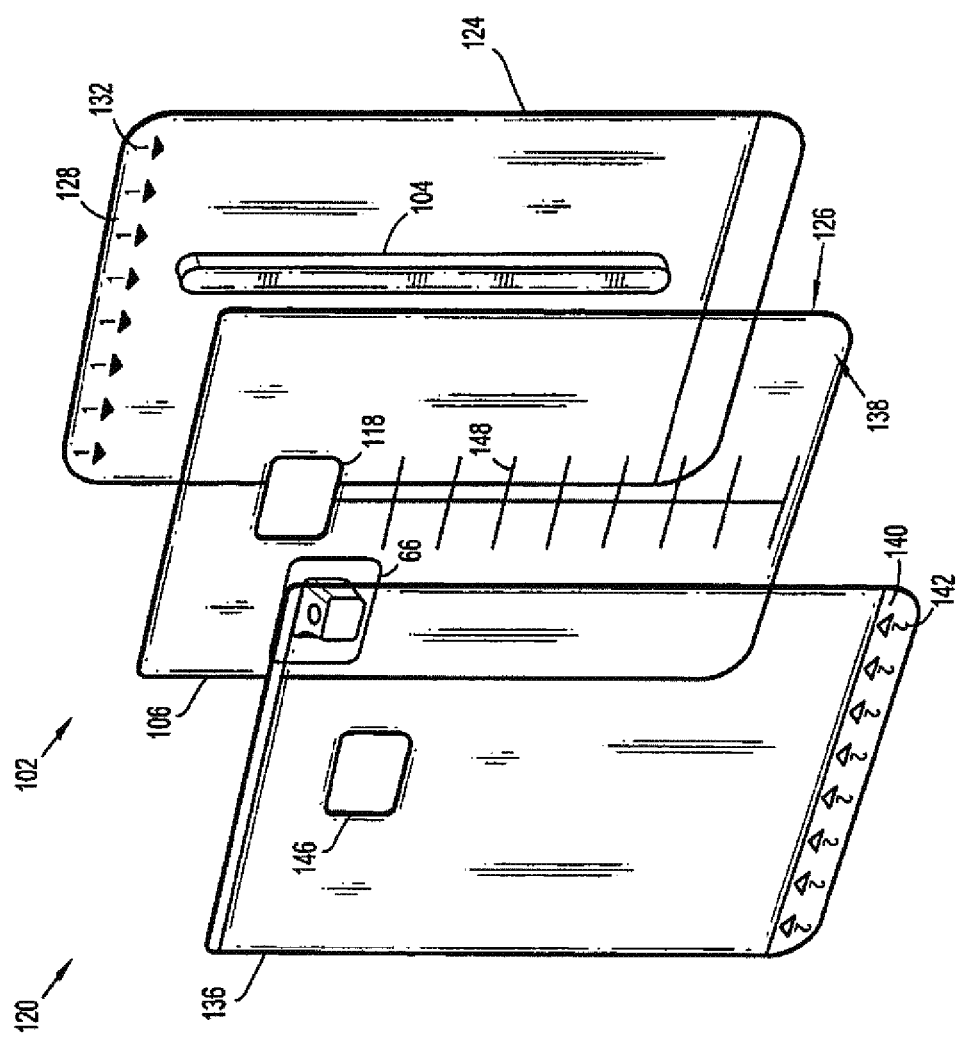
FIG. 11 is an exploded perspective view of a composite bridging dressing and delivery system in accordance with the present disclosure.

Referring now to FIG. 11, bridging dressing 102 is depicted as provided with a delivery system attached. While the composite dressing and delivery system 120 may be manufactured in any desired size or shape, the particular location of the wound "w" to be treated may prompt customization of each individual bridging dressing 102. As provided, composite dressing and delivery system 120 may be generally rectangular having a length of about 6 inches and a width of about 4 inches as shown. The composite dressing and delivery system 120 may be provided with a greater length than is anticipated to be necessary to permit the bridging dressing 102 to be cut to length at the time of application.

A backing layer 124 has a firm but releasable affinity for the adhesively coated lower surface 126 of the wick cover 106. Backing layer 124 covers the adhesive coating on the wick cover 106 and maintains the wick 104 in position against the lower surface 126 wick cover 106. The backing layer 124 includes a peripheral region 128 that extends substantially beyond at least one edge of the wick cover 106. Peripheral region 128 thus provides a gripping surface to facilitate the separation of the backing layer 124 from the wick cover 106. Peripheral region 128 includes an indicator, such as first numerical indicator 132, printed or otherwise applied thereto. First numerical indicator 132 provides a prominent visual queue to indicate the order in which the layers of the composite dressing and delivery system 120 should be separated.

A delivery layer 136 is adhered to an upper surface 138 of the wick cover 106 in a releasable manner. Delivery layer 136 is substantially rigid in relation to wick cover 106 to maintain the wick cover 106 in a relatively smooth and unwrinkled configuration while the wick layer 106 is applied over the lining 103 positioned to cover the skin "s" and/or the cover layer 24 (FIG. 10A). Delivery layer 136 is, however, sufficiently flexible to conform to irregular contours of the skin "s" such that the wick cover 106 may be pressed onto the skin "s" and/or the cover layer 24 to form a substantially fluid tight seal therewith. Thereafter, the delivery layer 136 may be separated from the wick cover 106.

Preferably, both delivery layer 136 and upper surface 138 are non-adhesive, and may be adhered by heat lamination contact or similar means. Alternately, the delivery layer may include an adhesive to provide appropriate adhesion to the cover layer during application. A peripheral region 140 of delivery layer 136 overlies wick cover 106, but is not adhered to wick cover 106. Peripheral region 140 thus provides a gripping surface to facilitate separation of the delivery layer 106 from the dressing layer 102. An indicator such as second numerical indicator 142 is positioned on the peripheral region 140 to indicate the order in which the layers of the composite dressing and delivery system 120 should be separated. Delivery layer 136 also includes a central opening 146 to accommodate fluid port 66. Fluid port 66 may be adhered to the upper surface 138, the lower surface 126, or removed all together.

In use, a bridging dressing 102 may be applied subsequent to the application of a cover layer 24 to a wound "w" (FIG. 10A). Once the desired length of the bridging dressing 102 is determined, the composite dressing and delivery system 120 may be cut to length. Indicia such as rule marks 148 may be printed or otherwise applied to the wick cover 106 to facilitate customizing the length of the bridging dressing 102. Alternatively, indicia may be applied to the backing layer 124 or the delivery layer 136, particularly when these layers are substantially transparent.

While the disclosure has been illustrated and described, it is not intended to be limited to the details shown, since various modifications and substitutions can be made without departing in any way from the spirit of the present disclosure. For example, in the embodiment of FIG. 1, the vacuum source 50 may be optional whereby wound exudate is conveyed through exudate tube via gravity, wicking or the like. In the embodiment of FIG. 2, the canister 52 may be optional whereby the exudate is contained within the exudate tube. In this embodiment, a filter or check valve may be utilized to prevent fluid communication into the vacuum source. It is further envisioned that a check valve could be positioned adjacent the wound end of exudate conduit to prevent fluid regress into the wound area. As such, further modifications and equivalents of the disclosure can occur to persons skilled in the art, and all such modifications and equivalents are intended to be within the spirit and scope of the disclosure as defined by the following claims.

What is claimed is:

1. A negative pressure wound dressing apparatus comprising:
    a wound dressing comprising a cover layer configured to define a reservoir over a wound in which a negative pressure can be maintained by forming a substantially fluid-tight seal around the wound, the cover layer comprising an aperture therein through which negative pressure can be applied to the reservoir;
    an elongate conduit having a first end, a second end, and a lumen, the first end configured to form a substantially fluid tight seal over the aperture in the cover layer, the second end including an aperture therein through which negative pressure can be applied to the lumen, wherein the conduit comprises an upper surface and an opposite, wound facing lower surface, wherein a portion of the lower surface is configured to contact the cover layer, and wherein the elongate conduit has a generally flattened, planar profile;
    a fibrous core disposed within the lumen of the conduit and extending along substantially the entire length of the conduit, wherein the fibrous core comprises a knitted nylon material defining an elongate sleeve having a length extending along the length of the fibrous core and wherein the fibrous core has a first end and a second end opposite from the first end, the first end configured to be in fluid communication with the reservoir through the aperture in the cover layer; and
    a connection member coupled to the conduit and in fluid communication with the second end of the fibrous core through the aperture in the second end of the conduit, the connection member configured to be in fluid communication with a vacuum source and further comprising a check valve disposed within the connection member, and the connection member is configured to be directly or indirectly connected to the vacuum source without a collection canister configured to collect fluid.

2. The negative pressure wound dressing apparatus of claim 1, wherein the fibrous core comprises a bundle of fibers.

3. The negative pressure wound dressing apparatus of claim 1, wherein the fibrous core comprises at least one fiber having a round cross-section.

4. The negative pressure wound dressing apparatus of claim 1, wherein the fibrous core comprises a continuous fiber.

5. The negative pressure wound dressing apparatus of claim 1, wherein the fibrous core comprises at least one hydrophobic fiber.

6. The negative pressure wound dressing apparatus of claim 1, wherein the fibrous core comprises at least one hydrophilic fiber.

7. The negative pressure wound dressing apparatus of claim 1, wherein the knitted nylon material comprises nylon 6.

8. The negative pressure wound dressing apparatus of claim 1, wherein the conduit is moisture vapor permeable.

9. The negative pressure wound dressing apparatus of claim 1, wherein the conduit comprises a polymer.

10. The negative pressure wound dressing apparatus of claim 9, wherein the conduit comprises polyvinyl chloride.

11. The negative pressure wound dressing apparatus of claim 1, wherein the conduit is transparent.

12. The negative pressure wound dressing apparatus of claim 1, wherein the fibrous core is configured to provide patency to the conduit when negative pressure is applied to the conduit.

13. The negative pressure wound dressing apparatus of claim 1, wherein the fibrous core is configured to prevent kinking of the conduit.

14. The negative pressure wound dressing apparatus of claim 1, further comprising a filter configured to prevent contamination of the vacuum source.

15. The negative pressure wound dressing apparatus of claim 1, further comprising an adhesive coated thin film disposed between the elongate conduit and the cover layer and configured to attach the elongate conduit to the cover layer.

16. A negative pressure wound therapy dressing comprising a drainage tube, wherein the drainage tube comprises a tube knitted or braided from a fiber, and wherein a sheath surrounds the knitted or braided tube.

17. The negative pressure wound therapy dressing of claim 16, wherein the sheath is moisture vapor permeable.

18. The negative pressure wound therapy dressing of claim 16, wherein the tube is a knitted tube.

19. The negative pressure wound therapy dressing of claim 16, wherein the fiber is a polyester, polyamide, polyethylene, polypropylene or polybutylene terephthalate fiber.

20. The negative pressure wound therapy dressing of claim 16, wherein the sheath comprises one or more layers.

21. The negative pressure wound therapy dressing of claim 20, wherein the knitted or braided tube is sandwiched between two layers of the sheath.

22. The negative pressure wound therapy dressing of claim 16, wherein the sheath is a polyurethane sheath.

23. The negative pressure wound therapy dressing of claim 16, wherein one end of the drainage tube forms an integral tab by which the drainage tube can be attached to the dressing.

24. The negative pressure wound therapy dressing of claim 16, wherein one end of the drainage tube is adapted for connection to a source of negative pressure.

* * * * *

UNITED STATES PATENT AND TRADEMARK OFFICE
CERTIFICATE OF CORRECTION

PATENT NO. : 10,406,036 B2
APPLICATION NO. : 15/856007
DATED : September 10, 2019
INVENTOR(S) : Richard M. Braga It is certified that error appears in the above-identified patent and that said Letters Patent is hereby corrected as shown below:

On the Title Page

On Page 4, Column 2, Item (56), Line 10, under U.S. Patent Documents, change "Risks," to --Risk,--.

On Page 8, Column 2, Item (56), Line 18, under Other Publications, change "Khirugii," to --Khirurgii,--.

On Page 8, Column 2, Item (56), Line 24, under Other Publications, change "Khirugii," to --Khirurgii,--.

On Page 8, Column 2, Item (56), Line 26, under Other Publications, change "Vesnik" to --Vestnik--.

In the Specification

In Column 8, Line 61, change "etheylene-" to --ethylene- --.

In Column 10, Line 28, change "antiobiotics," to --antibiotics,--.

In Column 10, Lines 37-38, change "floropolymers" to --fluoropolymers--.

In Column 13, Line 36, change "kitted" to --knitted--.

In Column 13, Line 55, after "the" delete "a".

Signed and Sealed this
Twelfth Day of November, 2019

Andrei Iancu
*Director of the United States Patent and Trademark Office*